United States Patent
Centen

(10) Patent No.: US 10,543,147 B2
(45) Date of Patent: Jan. 28, 2020

(54) OPTICAL TECHNIQUES FOR THE MEASUREMENT OF CHEST COMPRESSION DEPTH AND OTHER PARAMETERS DURING CPR

(71) Applicant: PHYSIO-CONTROL CANADA SALES LTD., Mississauga (CA)

(72) Inventor: Corey James Centen, Ottawa (CA)

(73) Assignee: PHYSIO-CONTROL CANADA SALES LTD., Mississauga, Ontario (CA)

( * ) Notice: Subject to any disclaimer, the term of this patent is extended or adjusted under 35 U.S.C. 154(b) by 90 days.

(21) Appl. No.: 15/403,110

(22) Filed: Jan. 10, 2017

(65) Prior Publication Data

US 2017/0143584 A1 May 25, 2017

Related U.S. Application Data

(63) Continuation of application No. 12/841,952, filed on Jul. 22, 2010.

(Continued)

(51) Int. Cl.
*A61B 5/00* (2006.01)
*A61B 5/113* (2006.01)
(Continued)

(52) U.S. Cl.
CPC ......... *A61H 31/005* (2013.01); *A61B 5/0064* (2013.01); *A61B 5/113* (2013.01);
(Continued)

(58) Field of Classification Search
CPC .......... A61H 31/005; A61H 2201/5092; A61N 1/3925; A61N 1/3993; G06T 7/20; G06T 7/0012
See application file for complete search history.

(56) References Cited

U.S. PATENT DOCUMENTS

| 4,314,251 A | 2/1982 | Raab |
| 5,239,988 A * | 8/1993 | Swanson ............... A61H 31/005 |
| | | 434/265 |

(Continued)

FOREIGN PATENT DOCUMENTS

| EP | 1350466 | 10/2003 |
| EP | 1491175 | 12/2004 |

(Continued)

OTHER PUBLICATIONS

International Search Report issued in International Application No. PCT/CA2010/000330, dated Jul. 2, 2010, 4 pages.

(Continued)

*Primary Examiner* — Jacqueline Cheng
*Assistant Examiner* — Tho Q Tran
(74) *Attorney, Agent, or Firm* — Lane Powell PC

(57) ABSTRACT

Embodiments of the present invention are related to a method and device for the determination and calculation of the depth of chest compressions during the administration of cardiopulmonary resuscitation (CPR). Embodiments use an optical sensor to monitor the distance that a victim's chest is displaced during each compression throughout the administration of CPR. The optical sensor is most commonly an image sensor such as a CMOS or CCD sensor, and more specifically a CMOS image sensor capable of three-dimensional imaging based on the time-of-flight principle. An infrared emitter may illuminate the victim's body and any visible piece of ground beside the victim. As the infrared light interacts with any surfaces it encounters, it is reflected and returns to the image sensor where the time of flight of the infrared light is calculated for every pixel in the image sensor. The distance data is used to gauge the effective displacement of the victim's chest. The optical sensors can be used to visualize the size of a patient and immediately (Continued)

SENSOR AFFIXED TO
ARM OF RESCUER gauge the body type and instruct the user accordingly. Furthermore, optical measurement techniques can be used to accurately measure chest rise during artificial respiration and ensure that proper ventilation is being administered in between compressions. In addition, optical measurements of the chest of the victim and the hands of the rescuer can be used to help ensure that the rescuer has positioned his or her hands in the anatomically correct location for effective CPR.

20 Claims, 22 Drawing Sheets

Related U.S. Application Data

(60) Provisional application No. 61/227,637, filed on Jul. 22, 2009.

(51) Int. Cl.
| | |
|---|---|
| G06T 7/60 | (2017.01) |
| A61N 1/39 | (2006.01) |
| G06T 7/00 | (2017.01) |
| G06T 7/20 | (2017.01) |
| A61H 31/00 | (2006.01) |
| A61N 1/04 | (2006.01) |
| G09B 23/28 | (2006.01) |
| G06T 7/269 | (2017.01) |

(52) U.S. Cl.
CPC ......... *A61N 1/0472* (2013.01); *A61N 1/3925* (2013.01); *A61N 1/3993* (2013.01); *G06T 7/0012* (2013.01); *G06T 7/20* (2013.01); *G06T 7/269* (2017.01); *G06T 7/60* (2013.01); *G09B 23/288* (2013.01); *A61H 2201/5058* (2013.01); *A61H 2201/5092* (2013.01); *A61N 1/046* (2013.01); *A61N 1/3968* (2013.01); *G06T 2207/10016* (2013.01); *G06T 2207/10028* (2013.01); *G06T 2207/30004* (2013.01)

(56) References Cited

U.S. PATENT DOCUMENTS

| | | | |
|---|---|---|---|
| 6,062,216 A | 5/2000 | Corn | |
| 6,323,942 B1 | 11/2001 | Bamji | |
| 6,351,671 B1 | 2/2002 | Myklebust et al. | |
| 6,827,695 B2* | 12/2004 | Palazzolo | A61B 5/04012 601/41 |
| 7,074,199 B2 | 7/2006 | Halperin et al. | |
| 7,402,996 B2 | 7/2008 | Arai et al. | |
| 2006/0247560 A1* | 11/2006 | Halperin | A61B 5/04017 601/41 |
| 2006/0270952 A1* | 11/2006 | Freeman | A61H 31/005 601/41 |
| 2007/0167999 A1 | 7/2007 | Breden et al. | |
| 2007/0276300 A1 | 11/2007 | Olson et al. | |
| 2008/0106739 A1* | 5/2008 | Sugiyama | G01D 5/34792 356/432 |
| 2008/0146974 A1* | 6/2008 | Lund | A61H 31/00 601/41 |
| 2008/0171311 A1 | 7/2008 | Centen et al. | |
| 2008/0204763 A1 | 8/2008 | Turbell et al. | |
| 2008/0243018 A1 | 10/2008 | Zuhars et al. | |
| 2010/0022904 A1 | 1/2010 | Centen | |
| 2010/0198118 A1* | 8/2010 | Itnati | A61H 31/004 601/41 |
| 2011/0301511 A1* | 12/2011 | Freeman | A61H 31/005 601/41 |

FOREIGN PATENT DOCUMENTS

| | | |
|---|---|---|
| EP | 1491176 | 12/2004 |
| EP | 1645841 | 4/2006 |
| EP | 1859770 | 11/2007 |
| WO | 2003101537 | 12/2003 |
| WO | 2004073797 | 9/2004 |
| WO | 2008059394 A1 | 5/2008 |
| WO | 2009156924 A1 | 12/2009 |
| WO | 2010009531 | 1/2010 |
| WO | 2010099628 | 9/2010 |

OTHER PUBLICATIONS

International Preliminary Report on Patentability issued in International Application No. PCT/US2010/042954, dated Jan. 24, 2012, 12 pages.

International Search Report and Written Opinion issued in International Application No. PCT/US2010/042954, dated Jan. 25, 2011, 20 pages.

\* cited by examiner

IMAGE SENSOR

FIG. 2　TIME OF FLIGHT

| 6 | 2 | 4 | 5 | 7 | 7 | 8 | 4 |
|---|---|---|---|---|---|---|---|
| 2 | 3 | 4 | 5 | 3 | 2 | 3 | 9 |
| 1 | 6 | 2 | 5 | 9 | 9 | 4 | 3 |
| 3 | 4 | 1 | 3 | 7 | 2 | 1 | 1 |
| 8 | 2 | 4 | 0 | 4 | 3 | 7 | 6 |
| 9 | 2 | 3 | 4 | 9 | 1 | 1 | 3 |
| 1 | 8 | 9 | 2 | 3 | 4 | 7 | 2 |
| 2 | 4 | 5 | 8 | 9 | 8 | 3 | 2 |

FIG. 3     <u>ARRAY VALUES</u>

COMPRESSION GRADIENT
REPRESENTATION

FIG. 5   WEARABLE SENSOR

FIG. 6   SENSOR HOUSING

FIG. 7  SENSOR SUPPORT STAND

FIG. 8                  EXTERNAL DEFIBRILLATOR

FIG. 9   PIVOT

FIG. 10  SENSOR AFFIXED TO ARM OF RESCUER

FIG. 11      COMPRESSION REGIONS

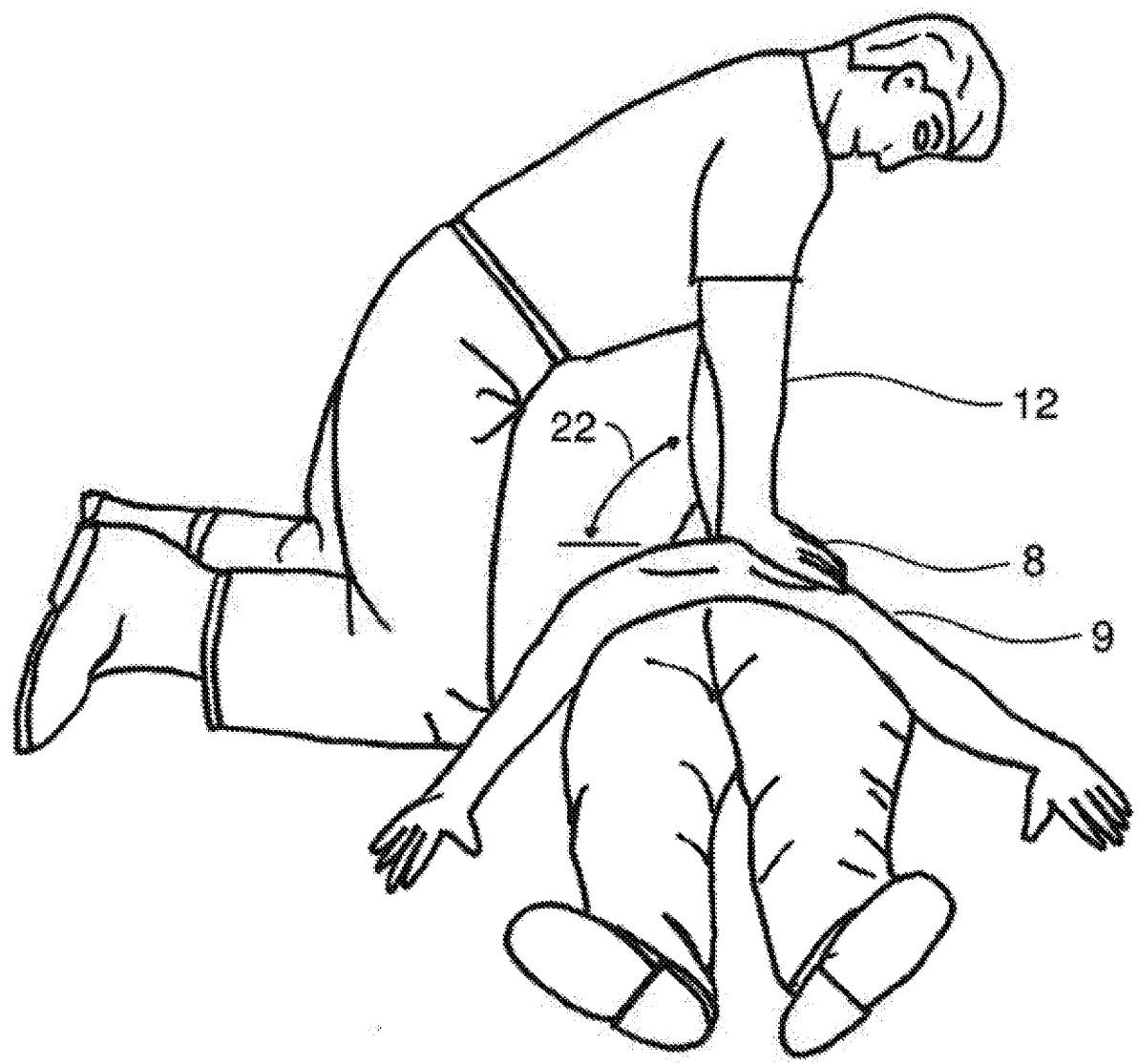
FIG. 13    RESCUE SCENE

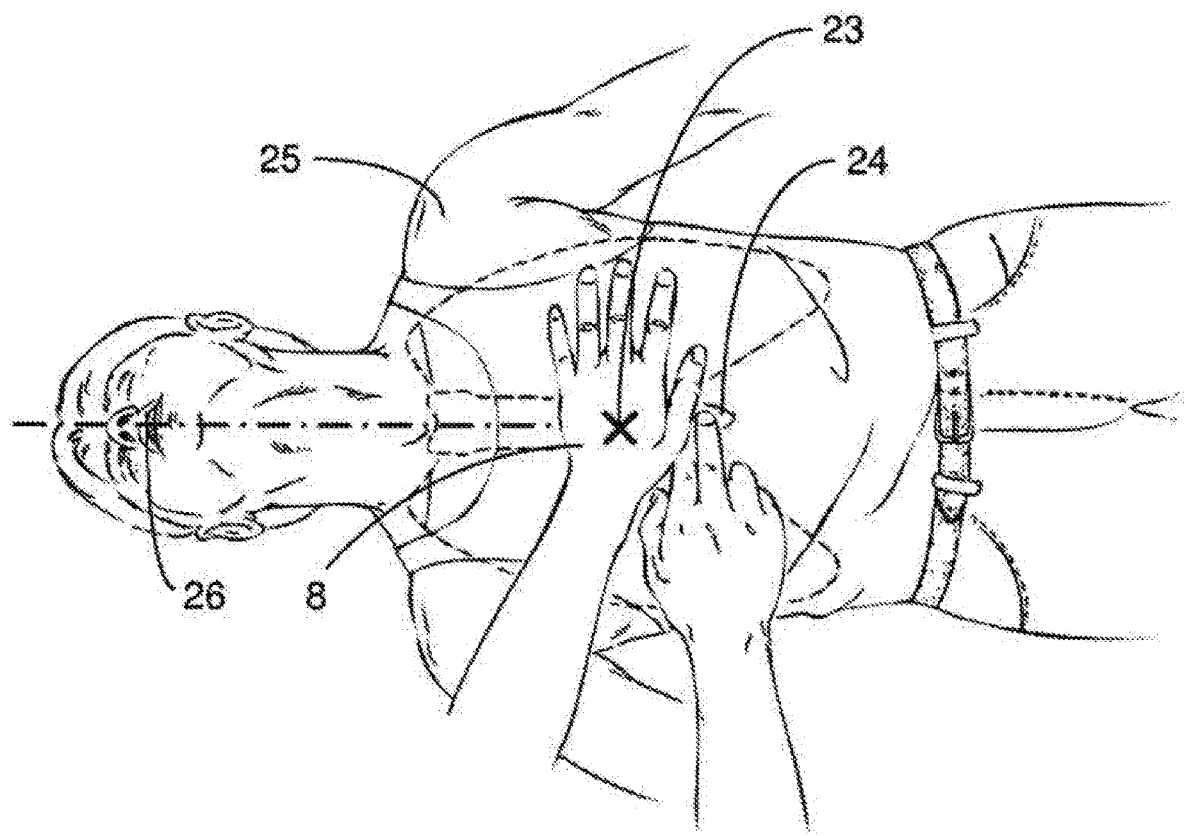
FIG. 14  HAND PLACEMENT

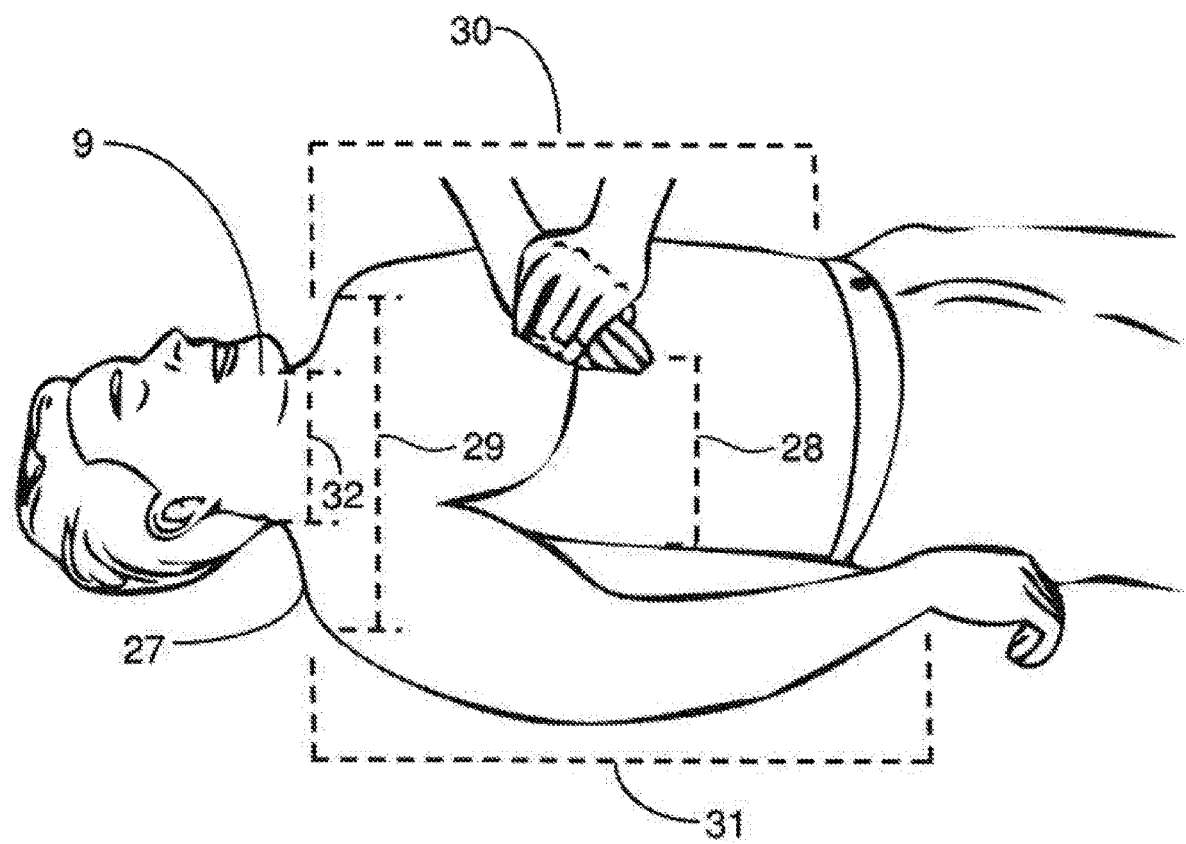
FIG. 15      MEASUREMENT AREAS

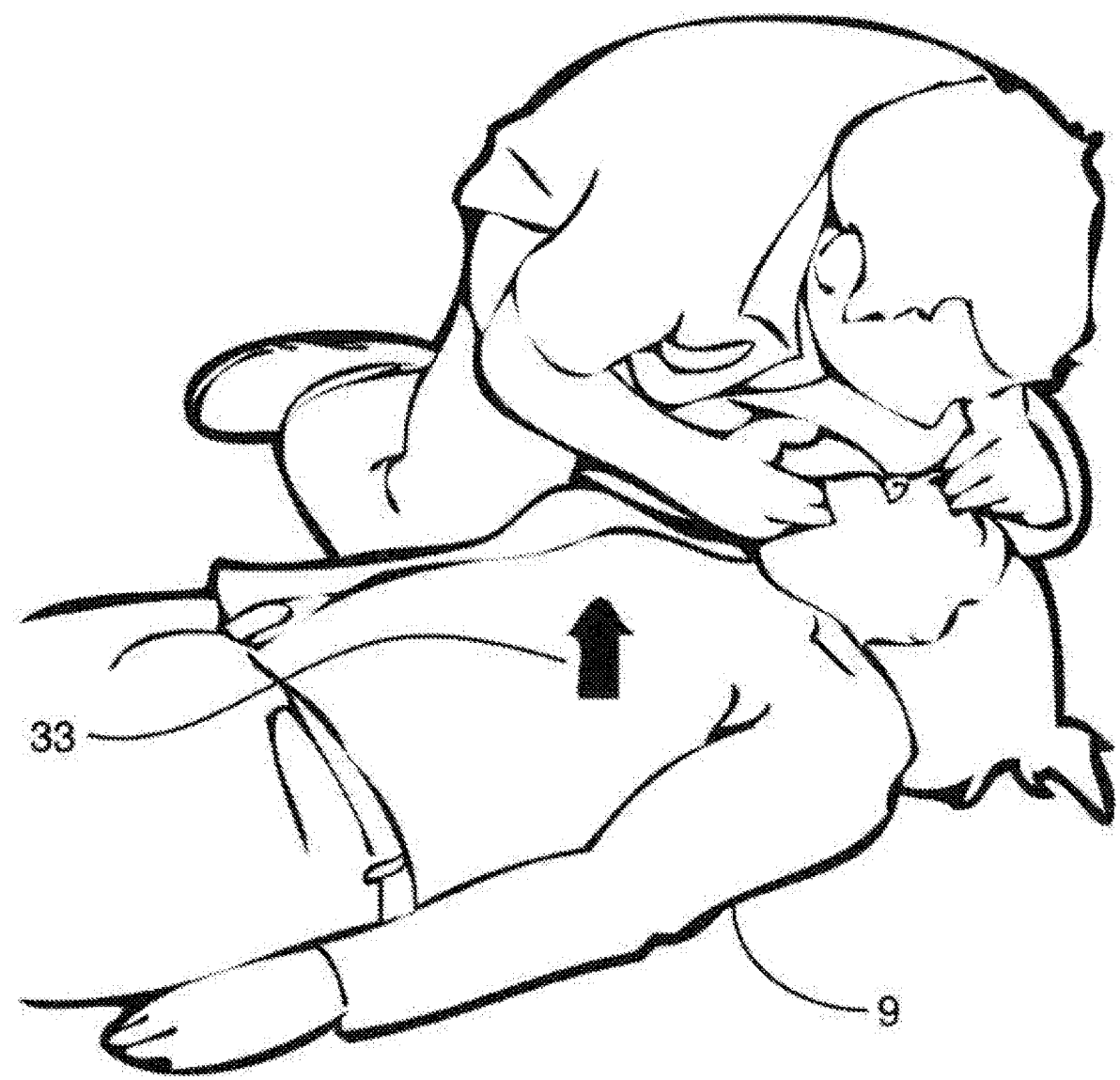
FIG. 16　　　RESCUE BREATHING

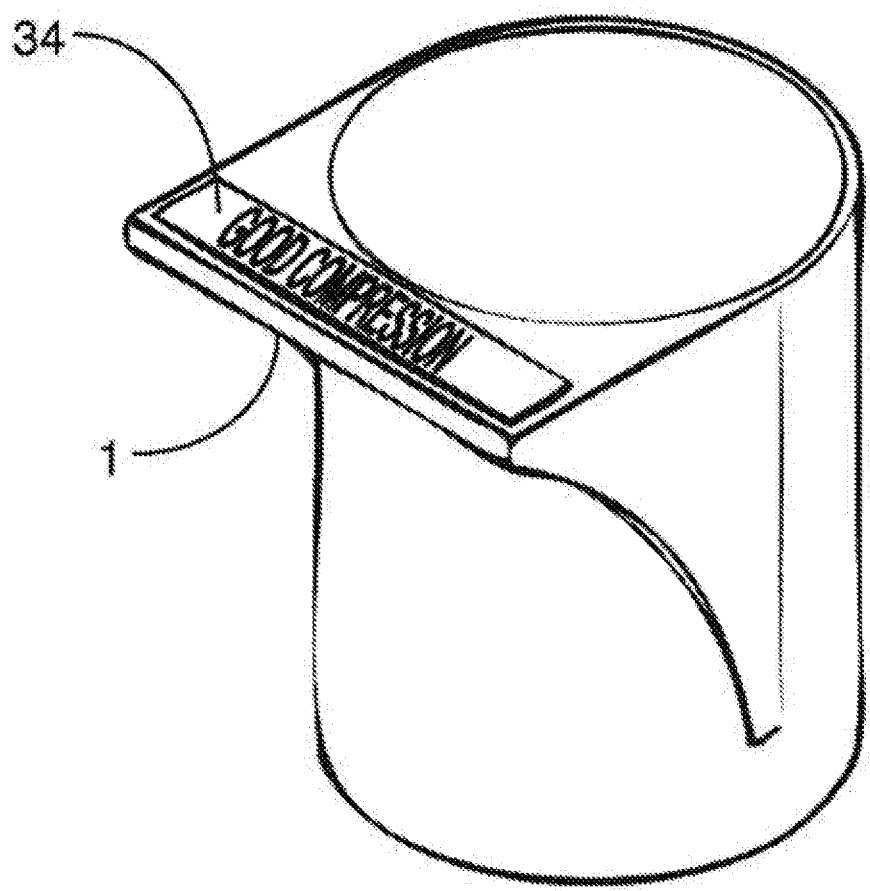
FIG. 17                  <u>ARM BAND</u>

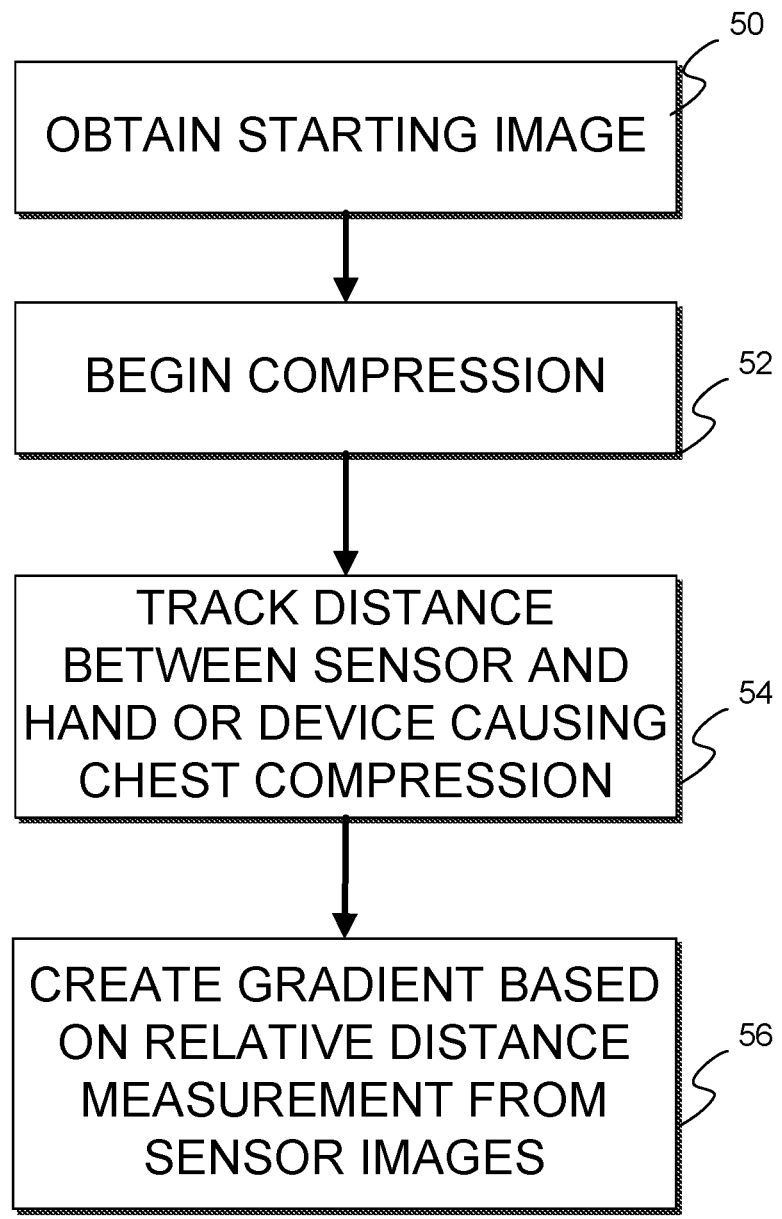
FIG. 18     METHODS

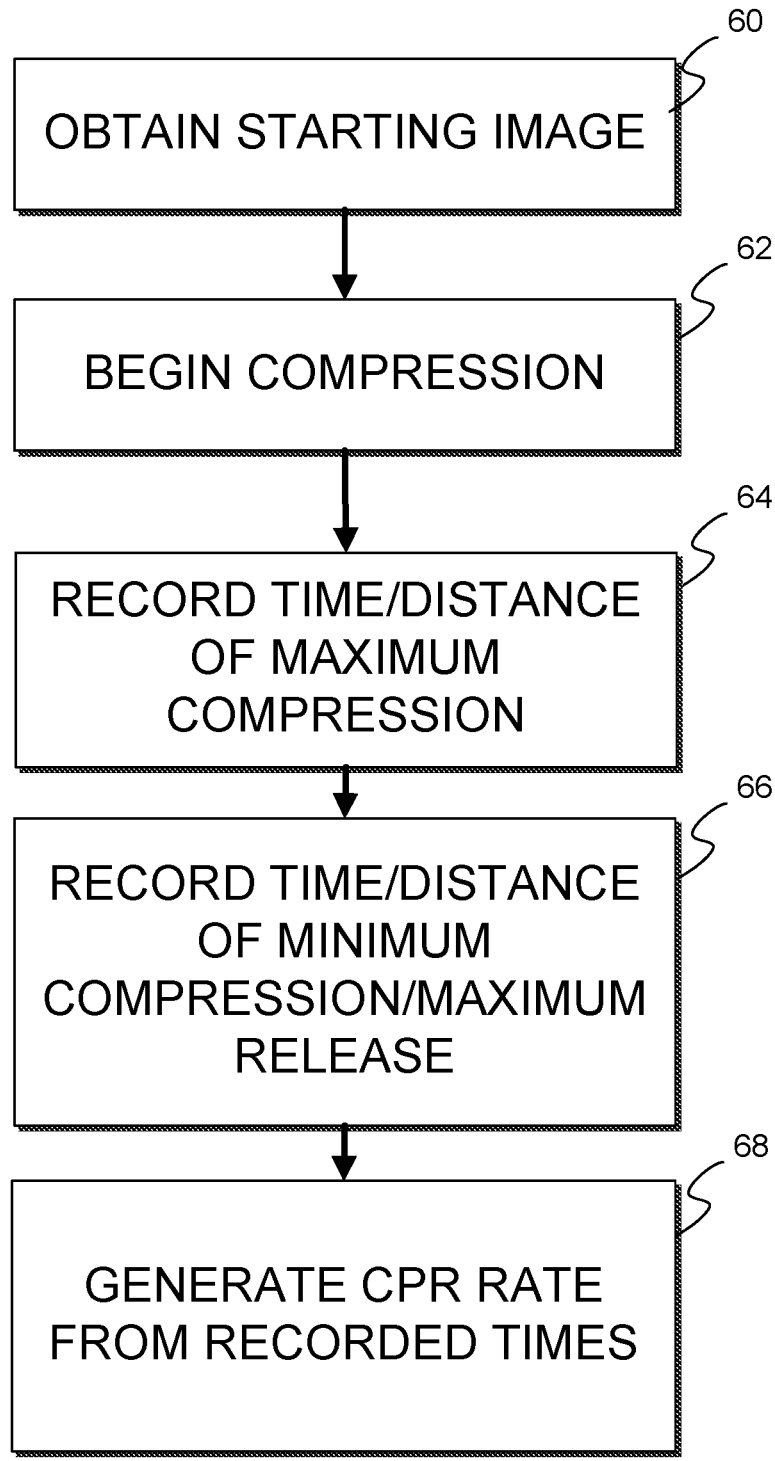
FIG. 19     METHODS

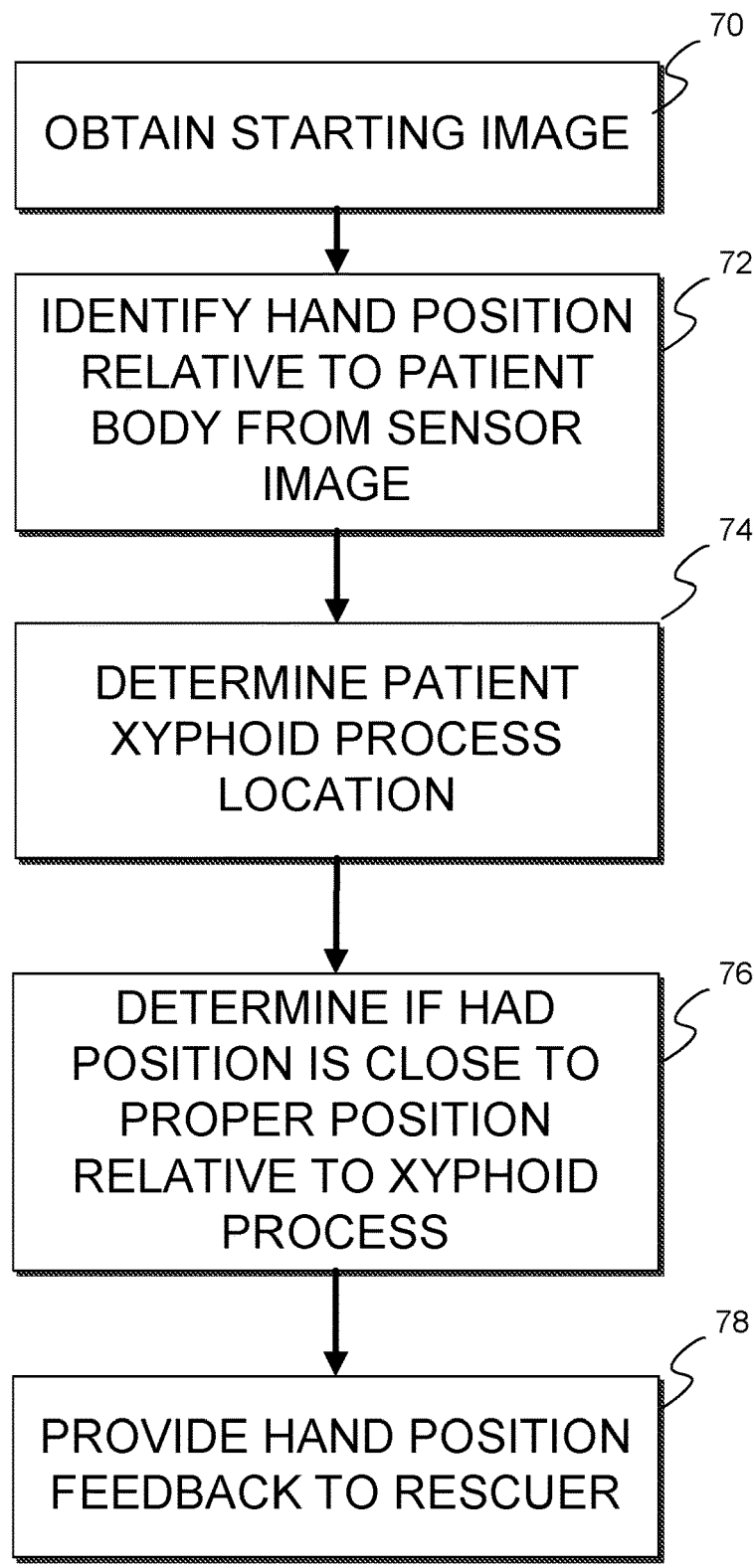
FIG. 20     METHODS

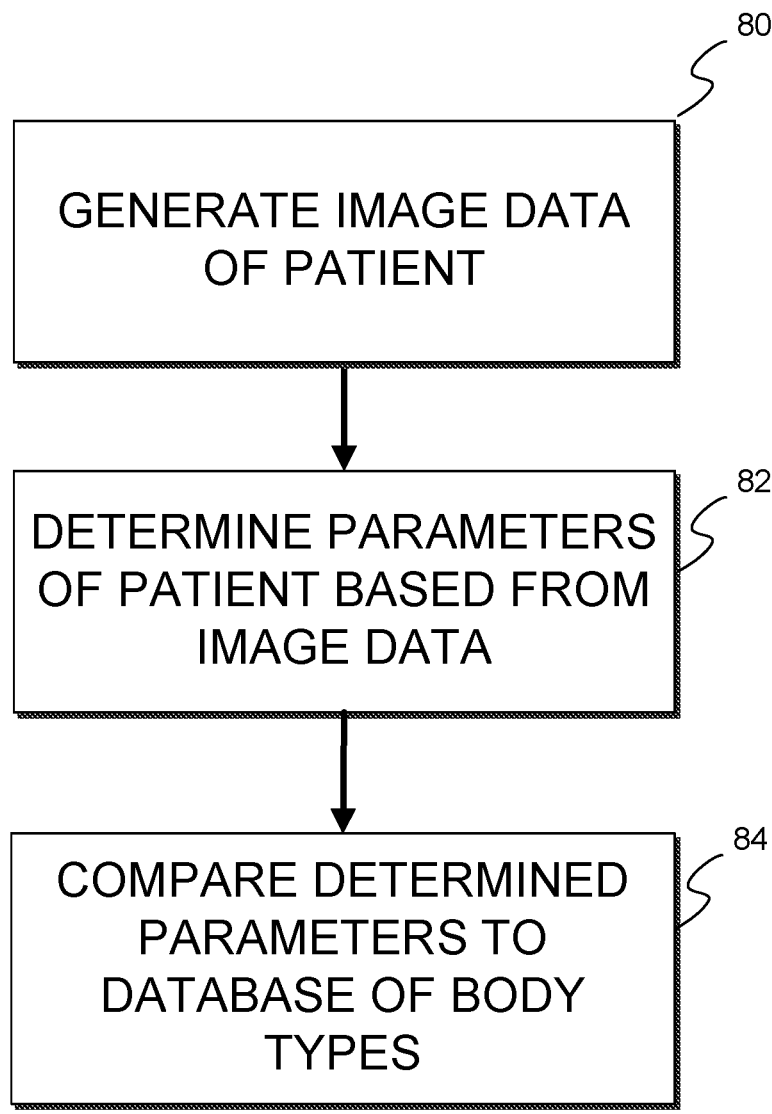
FIG. 21  METHODS

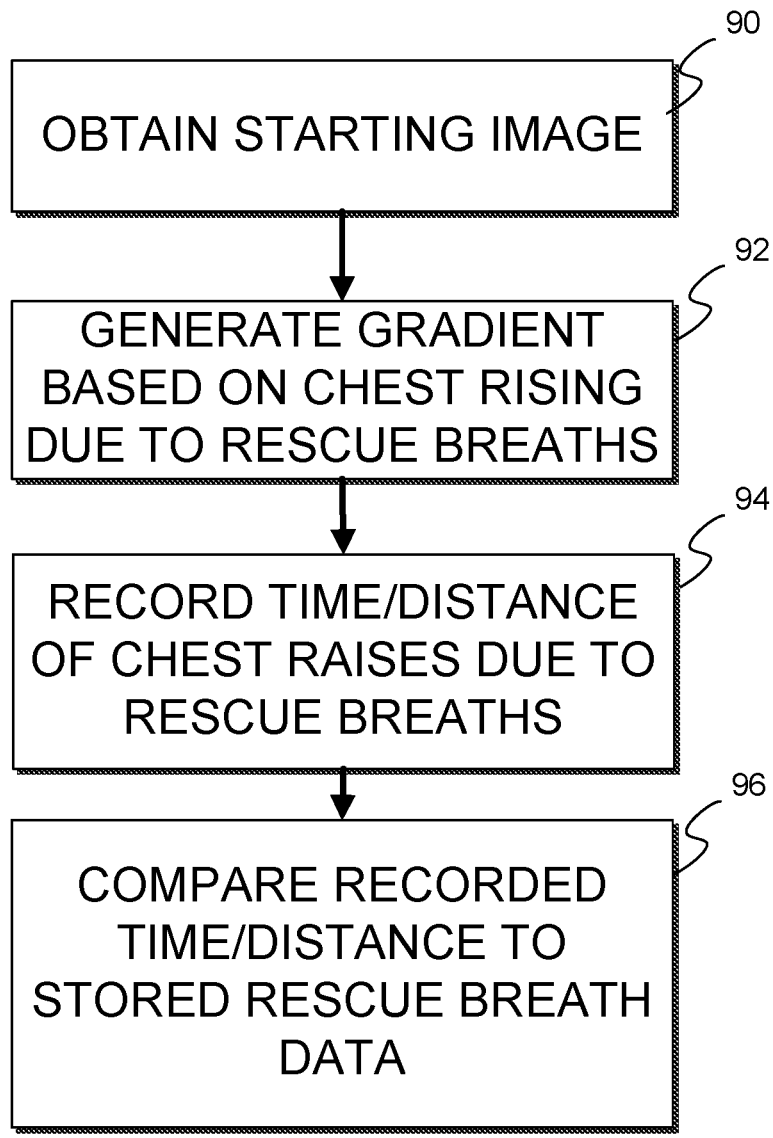
FIG. 22  METHODS

OPTICAL TECHNIQUES FOR THE MEASUREMENT OF CHEST COMPRESSION DEPTH AND OTHER PARAMETERS DURING CPR

CROSS REFERENCE TO RELATED APPLICATIONS

This application is a continuation of U.S. Non-Provisional application Ser. No. 12/841,952, filed Jul. 22, 2010, titled OPTICAL TECHNIQUES FOR THE MEASUREMENT OF CHEST COMPRESSION DEPTH AND OTHER PARAMETERS DURING CPR, which claims benefit from U.S. Provisional Application No. 61/227,637, filed Jul. 22, 2009, titled OPTICAL TECHNIQUES FOR THE MEASUREMENT OF CHEST COMPRESSION DEPTH AND OTHER PARAMETERS DURING CPR, the disclosures of both of which are incorporated herein by reference their entirety.

FIELD OF INVENTION

This disclosure generally relates to the measurement of chest compression depth during the administration of cardiopulmonary resuscitation (CPR), specifically to compression depth measurement by use of optical sensors.

BACKGROUND OF THE INVENTION

There are currently an estimated 40,000 incidences of cardiac arrest every year in Canada, most of which take place outside of hospital settings. The odds of an out-of-hospital cardiac arrest currently stand at approximately 5%. In the U.S., there are about 164 600 such instances each year, or about 0.55 per 1000 population. There is a desire to decrease these out-of hospital incidences of cardiac arrest. Certain places, such as sports arenas, and certain classes of individuals, such as the elderly, are at particular risk and in these places and for these people, a convenient solution may be the difference between survival and death.

Cardiopulmonary resuscitation (CPR) is a proven effective technique for medical and non-medical professionals to improve the chance of survival for patients experiencing cardiac failure. CPR forces blood through the circulatory system until professional medical help arrives, thereby maintaining oxygen distribution throughout the patient's body. However, the quality of CPR is often poor. Memory retention of proper CPR technique and protocol may be inadequate in most individuals and the anxiety of an emergency situation may confuse and hinder an individual in delivering proper treatment.

According to the journal of the American Medical Association (2005), cardiopulmonary resuscitation (CPR) is often performed inconsistently and inefficiently, resulting in preventable deaths. Mere months after the completion of standard CPR training and testing, an individual's competency at performing effective chest compressions often deteriorates significantly. This finding was found to hold true for untrained performers as well as trained professionals such as paramedics, nurses, and even physicians.

The International Liaison Committee on Resuscitation in 2005 described an effective method of administering CPR and the parameters associated with an effective technique. Parameters include chest compression rate and chest compression depth. Chest compression rate is defined as the number of compression delivered per minute. Chest compression depth is defined as displacement of the patient's sternum from its resting position. An effective compression rate may be 100 chest compressions per minute at a compression depth of about 4-5 cm. According to a 2005 study at Ulleval University Hospital in Norway, on average, compression rates were less then 90 compressions per minute and compression depth was too shallow for 37% of compressions.

According to the same study, CPR was often administered when unnecessary or was not administered when necessary. The study found that compressions were not delivered 48% of the time when cardiovascular circulation was absent.

Positioning of the hands is another parameter that may be considered when delivering CPR. It has been found that an effective position for the hands during compression is approximately two inches above the base of the sternum. Hand positioning for effective CPR may be different depending on the patient. For example, for performing CPR on an infant, an effective position may be to use two fingers over the sternum.

Other studies have found similar deficiencies in the delivery of CPR. A 2005 study from the University of Chicago found that 36.9% of the time, fewer than 80 compressions per minute where given, and 21.7% of the time, fewer than 70 compressions per minute were given. The chest compression rate was found to directly correlate to the spontaneous return of circulation after cardiac arrest, so it is very important that the optimum rate be achieved for maximum chances of patient survival.

In addition to too shallow compressions, too forceful compressions may also be problematic. Some injuries related to CPR are injury to the patient in the form of cracked ribs or cartilage separation. Such consequences may be due to excessive force or compression depth. Once again, lack of practice may be responsible for these injuries.

Therefore, a device to facilitate the proper delivery of CPR in an emergency is desired. Furthermore, a device that can also be used in objectively training and testing an individual may be useful for the CPR training process and protocol retention.

Current solutions in emergency cardiac care mostly focus on in-hospital treatment or appeal mostly to medical professionals. CPR assist devices that tether to defibrillators can be found in hospitals. However, these devices are often expensive and inaccessible to the lay individual who does not have a defibrillator on hand or cannot operate such a device. Furthermore, such devices are often not portable nor are they easily accessible. Simple devices with illuminated bar graph or LED displays indicating compression force are often cumbersome in design and non-intuitive in use. Such a device may be uncomfortable to the patient and user and often has minimal data output. Thus, misuse of such a device is most likely rendering it a hindrance rather than an aid.

There are currently mechanical systems for the delivery of CPR that may be used in a hospital setting. Chest compression may be delivered through a mechanism including mechanical movement (e.g., piston movement or motor movement). One such device is the AUTOPULSE by Revivant Corp, which has a computer-controlled motor attached to a wide chest band that compresses the chest, forcing blood to the brain when the heart has stopped beating. Such a device is cumbersome and heavy to transport, requires time to set up and activate and is expensive.

U.S. Pat. No. 6,351,671 discloses a device that measures the chest impedance of a victim as well as the force of active chest compressions. From these calculations, the device indicates to the user when a successful compression has been completed. However, this technology requires defibrillator pads to be placed across the chest of the victim and is, consequently, relatively time consuming to activate. The commercially available device, Q-CPR by Phillips Medical, must be attached to an expensive hospital-grade defibrillator making it expensive, heavy and inaccessible to the lay user.

U.S. Pat. No. 7,074,199 discloses the use of an accelerometer for the measurement of compression depth. Any acceleration data from accelerometers used to measure the depth of chest compression during CPR is prone to cumulative errors. Consequently, these sensors are not suitable for highly accurate or detailed data collection regarding CPR parameters and can only be relied on for approximate depth values. Furthermore, the use of an accelerometer in a CPR monitoring device without an external reference is prone to error if the patient or rescuer is mobile. For example, if the patient is being medically transported in an ambulance, helicopter or on a gurney, the accelerometer is unable to differentiate between the external movement of the patient and the compressions of the chest. In any type of non-stationary environment, an accelerometer based device is unreliable and ineffective. The use of an accelerometer to calculate compression depth also relies on complicated and error-prone calculations to compensate for the angle and tilt of the compression device. If the accelerometer is not perfectly level on the chest of the victim and its movement is not perfectly vertical, errors will accumulate and must be accounted for by the angle of the two horizontal axes. Certain commercial products currently use accelerometer technology, such as the AED PLUS D-PADZ from Zoll Medical, in which the accelerometer is embedded into the pads of the defibrillator. Due to the additional circuitry and sensory within them, these defibrillator pads are substantially more expensive and must be disposed of after each use. Therefore, relatively expensive sensory must be routinely discarded due to the design of the product.

Currently, a widely used technology in the training environment is the CPR mannequin. One commonly used version is the RESUSCI-ANNE doll manufactured by Laerdal Medical Inc. The RESUSCI-ANNE doll allows an individual to practice his or her CPR while being subjectively monitored by an instructor. This technique relies on the observational skills of the instructor and thus may be prone to human error. Furthermore, for effective training to take place, each student must be observed separately thereby occupying a significant amount of time and decreasing the number of students who can be trained at one time. In addition, Actar Airforce Inc. develops ACTAR mannequins providing limited feedback that are currently also used in CPR training. Again, such mannequins rely on close monitoring by the instructor to be effective for training.

It would still be desirable to provide an easy-to-use and inexpensive device to accurately measure relevant CPR parameters such as compression depth and rate absent of the problems in the aforementioned technologies.

SUMMARY

Embodiments of invention are directed to methods and devices for the determination and calculation of the depth of chest compressions during the administration of cardiopulmonary resuscitation (CPR). Embodiments include the use of optical sensors to monitor the distance that a victim's chest is displaced during each compression throughout the administration of CPR. The optical sensor is most commonly an image sensor such as CMOS or CCD sensor, and more, in some specific embodiments can be a CMOS image sensor capable of three-dimensional imaging based on the time-of-flight principle. However, other embodiments may include other traditional optical sensors such as infrared, optical proximity, LED, optical flow or laser-based technologies. Those skilled in the art will appreciate that, while the preferred sensor is desirably a time-of-flight depth sensor, this is not a requirement of the invention. Other sensors capable of detecting the position of an object in three-dimensional space may be used without departing from the spirit of the inventive principles disclosed herein.

In the case of image sensors, the sensor may be placed on the rescuer or in a device external to the rescuer, such as a block or pad. If placed on the rescuer, the sensor may be located in any of a number of positions. In one embodiment, the sensor may be placed in a glove worn by the rescuer and the glove may position the sensor on the posterior surface of the forearm. The image sensor may be directed so that the pixels of the sensor are pointed downward enabling visualization of a portion of the victim's body as well as the ground beneath the victim. An infrared emitter may be positioned adjacent to the image sensor to illuminate the victim's body and any visible piece of ground beside the victim. As the infrared light interacts with the surfaces it encounters, it is reflected and returns to the image sensor where the time of flight of the infrared light is calculated for every pixel in the image sensor. This distance data is used to gauge the effective displacement of the rescuer's hand and arm relative to a non-moving surface such as the ground or a stationary portion of the victim, such as the shoulders, head, neck, stomach or legs.

In another embodiment of the invention, an image sensor is placed on the posterior surface of the forearm but is positioned toward the rescuer's torso rather than the torso of the victim. The image sensor is configured so that it may determine the depth of a compression by monitoring the optical flow of its environment, such as the change in pattern of the rescuer's stationary upper body. The optical flow method can also be used to track changes in other stationary features of the rescuer's environment, such as walls or immobile objects, and relate these to the depth of each compression.

Rather than being configured within a wearable device on the rescuer, embodiments of the invention may also be incorporated into a block, pad or other device placed under the hands of the rescuer performing the CPR. The image or optical sensor may be directed toward the chest of the victim, toward the torso of the rescuer or toward the environment to track optical changes and relate these to the depth of each chest compression.

In another embodiment, the optical sensor may be placed on a device independent of the rescuer. The image sensor or optical sensor may be placed on a stationary support positioned above the chest of the victim and over the hands of the rescuer. The sensor may then determine the depth of each compression by reflecting infrared light from the victim and rescuer and using time-of-flight calculations or other techniques to gauge compression depth.

The use of optical compression depth techniques also has applications in CPR training. The device may be used to accurately gauge compression depth while training individuals in CPR. This technique is highly accurate and can be used to properly train individuals to administer CPR at the proper depth, a common problem plaguing many rescuers.

Furthermore, optical compression depth techniques have further advantages. Unlike the use of gyroscope or accelerometer based sensors, optical techniques do not suffer from cumulative error and do not rely on inertial measurements that can be affected by the surrounding environment. When using accelerometers, the victim and rescuer must not experience any external movement such as that caused by transport of the victim in an ambulance or helicopter. Such random and non-isolated movements of the patient will invalidate any measurements taken by inertial sensors. Furthermore, optical sensor techniques have the advantage of being useful in a wide-array of CPR related measurements not limited to compression depth. The optical sensors can be used to visualize the size of a patient and immediately gauge the body type and instruct the user accordingly. For instance, there is a significant difference between infant and adult CPR and automatic body type compensation algorithms are highly beneficial in a fast-moving emergency where every second matters. Furthermore, optical measurement techniques can be used to accurately measure chest rise during artificial respiration and ensure that proper ventilation is being administered in between compressions. In addition, optical measurements of the chest of the victim and the hands of the rescuer can help ensure that the rescuer has positioned his or her hands in the anatomically correct location for effective CPR.

Optical compression depth measurement techniques are a highly accurate and likely inexpensive method of determining compression depth during the administration of CPR. Optical methods do not suffer from the drawbacks of accelerometer-based techniques. They are inherently more accurate as they do not experience cumulative errors or inaccuracies due to movement of the victim or rescuer.

BRIEF DESCRIPTION OF THE DRAWINGS

Aspects of the present invention will be discussed in detail below, with reference to the drawings in which:

FIG. 13 shows a rescuer performing CPR with a proper compression angle of approximately ninety degrees according to embodiments of the invention;

FIG. 14 illustrates the proper placement of the rescuer's hands during the administration of CPR;

FIG. 15 illustrates the various measurements that may be carried out by a three dimensional image sensor on the victim's body according to embodiments of the invention;

FIG. 16 shows the direction of chest rise during the administration of rescue breathing;

FIG. 17 shows a wearable arm band that may house a three-dimensional image sensor according to embodiments of the invention; and FIGS. 18-22 illustrate various methods that may be performed according to embodiments of the invention.

DETAILED DESCRIPTION OF THE INVENTION

An image sensor is a device that converts an optical image to an electric signal. The two most widely recognized types of image sensors are the (Complementary Metal Oxide Semiconductor) CMOS and CCD (Charge Coupled Device) sensors. A CMOS chip is a type of active pixel sensor made using the CMOS semiconductor process. Extra circuitry next to each pixel sensor converts the light energy to a voltage. Additional circuitry on the chip converts the voltage to digital data. A CCD is an analog device. When light strikes the chip it is held as a small electrical charge in each pixel sensor. The charges are converted to voltage one pixel at a time as they are read from the chip. Additional circuitry in the camera converts the voltage into digital information.

Figure 1:
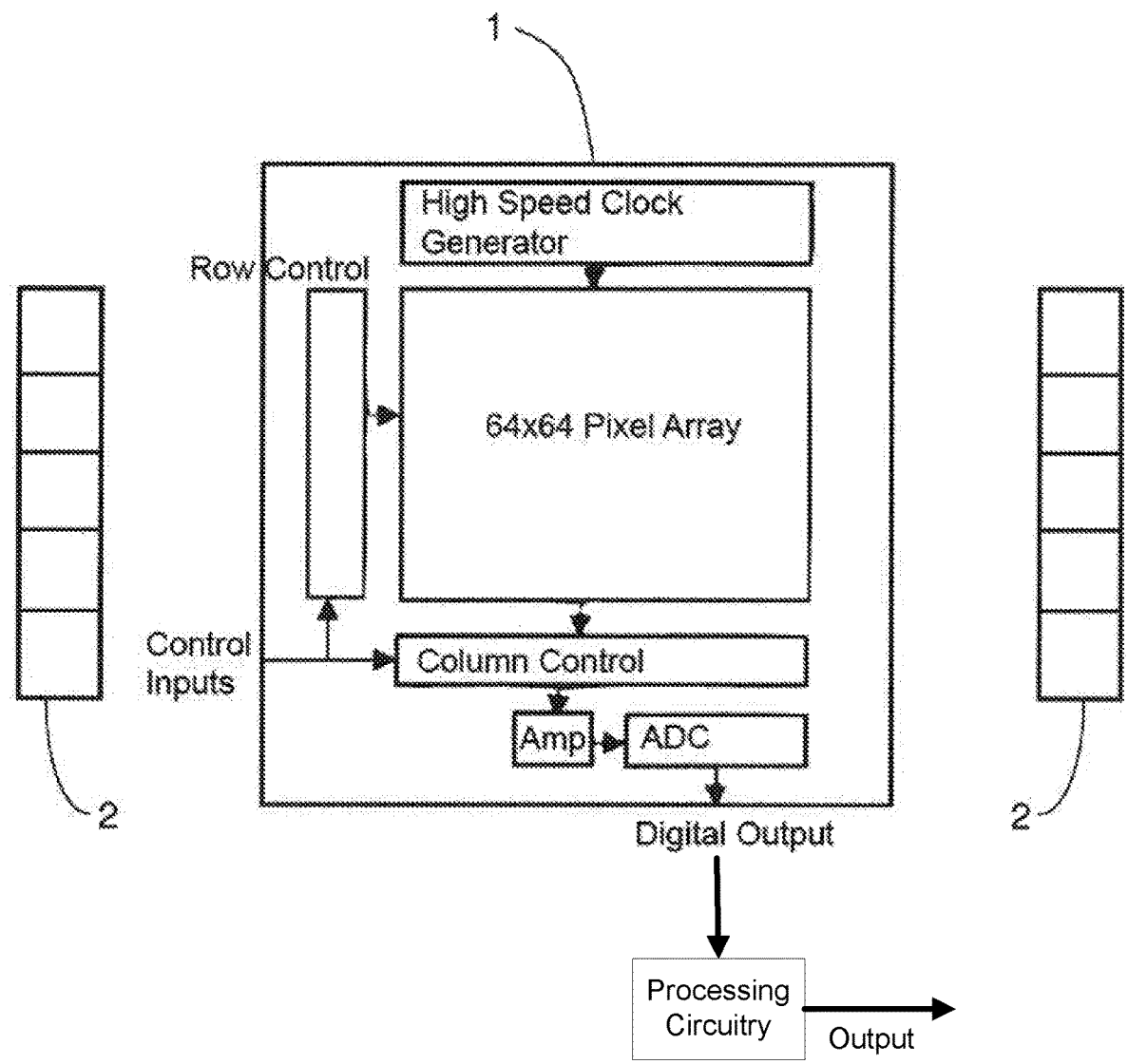
FIG. 1 shows a time-of-flight three-dimensional CMOS image sensor with infrared illumination sources according to embodiments of the invention.

A CMOS image sensor 1 is illustrated in FIG. 1 Along with an infrared illumination source 2, the image sensor 1 determines the three-dimensional characteristics of a scene by measuring the time-of-flight of the illumination from the infrared source 2. Recent advances have allowed one-chip solutions that enable the capturing and processing of real-time three dimensional images and video. The small CMOS sensor 1 determines the distance to objects in the environment with millimetre accuracy while maintaining fast frame rates. Such three-dimensional images are invaluable to areas requiring real-time precision depth or distance measurement. One application that can benefit enormously from such a technology is chest compression monitoring during the administration of CPR. Output from the sensor 1 may be passed to other processing circuitry known in the art to calculate desired outputs or control signals. For instance the processing circuitry may include timers, counters, Arithmetic Logic Units (ALUs), programmed processors etc. for generating the outputs used in other parts of the system. Conversely, some or all of these functions may take place on or in what is illustrated as the sensor 1.

One application of time-of-flight optical sensors in the monitoring of CPR is the accurate determination of chest compression depth. Other embodiments additionally determine other parameters useful in evaluating the efficacy of the CPR being performed. Time-of-flight optical sensors have a wide range of possibilities in CPR including determination of: compression rate, victim body type, efficient rescue breathing, hand positioning during compressions, and chest recoil. This new technology has the potential to revolutionize the delivery of CPR, making it an efficient and accurate procedure free from any significant human error.

DETERMINATION OF COMPRESSION DEPTH

A. Time-of-Flight Measurement

Figure 2:
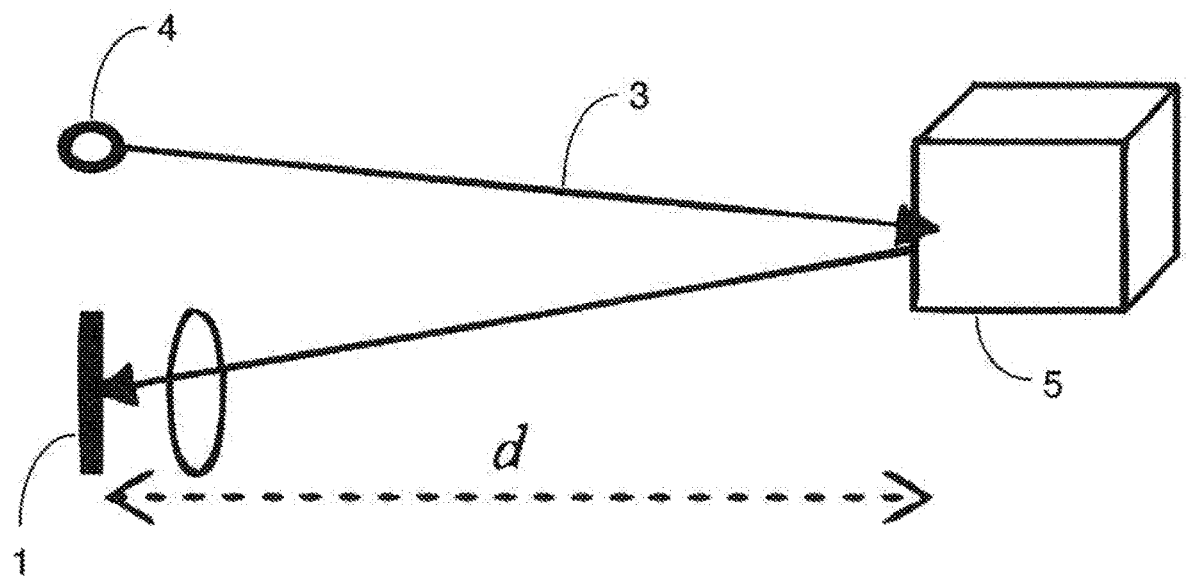
FIG. 2 illustrates the time-of-flight principle of operation for a three-dimensional image sensor that may be used in embodiments of the invention.
Figure 3:
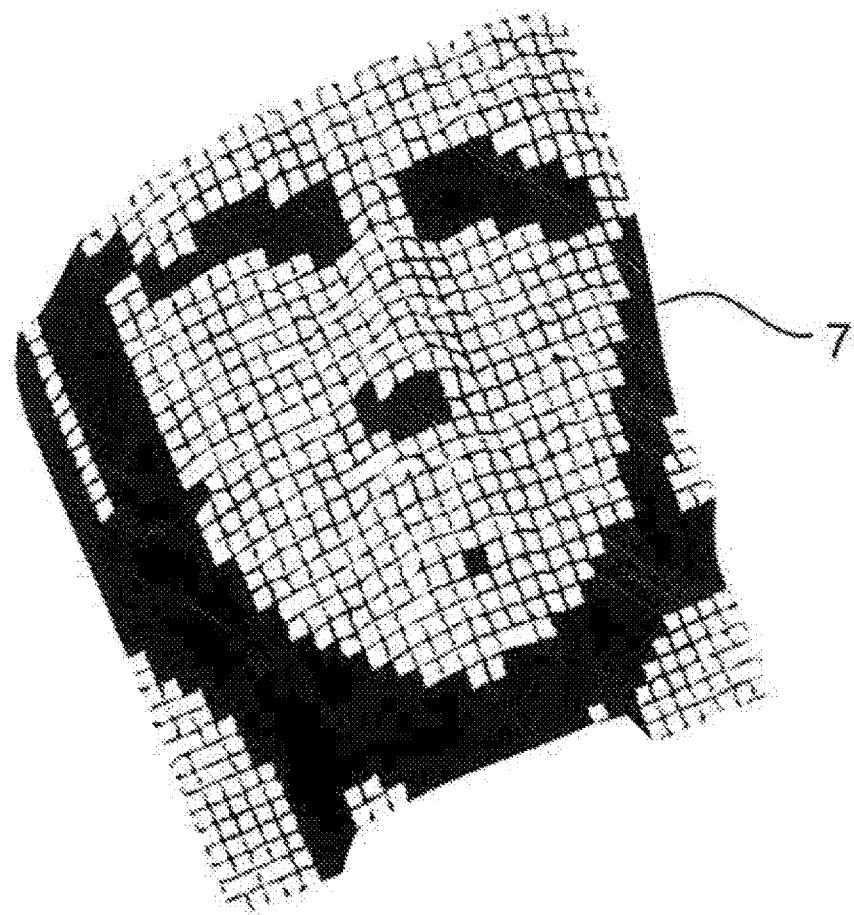
FIG. 3 depicts an array of values representing the distance of an object at each pixel of a three-dimensional image sensor, such as the image sensor of FIG. 1.

In a preferred embodiment, the present invention utilizes the CMOS image sensor 1, an illuminating source 2 such as an infrared light emitting diode (LED) and processing circuitry to compute compression depth. In this embodiment, the CMOS sensor 1 and accompanying circuitry function similar to radar. The distance to an object is calculated using a measurement of time that it takes an electronic burst of unobtrusive light or invisible (yet detectible) energy 3 to make the round trip from a transmitter 4 to the reflective object 5 and back as shown in FIG. 2. The image sensor 1 is completely or mostly immune to ambient light and is able to independently, or along with other circuitry, internally determine the length of time taken by the pulse to reflect back to each pixel, using high speed, on-chip timers or by simply measuring the number of returning photons. The result is an array of distances 6 that provides a mathematically accurate, dynamic relief map 7 of the surfaces being imaged as shown in FIG. 3. The image and distance information is then processed to further refine the three dimensional representation before being used to compute compression depth information.

Figure 4:
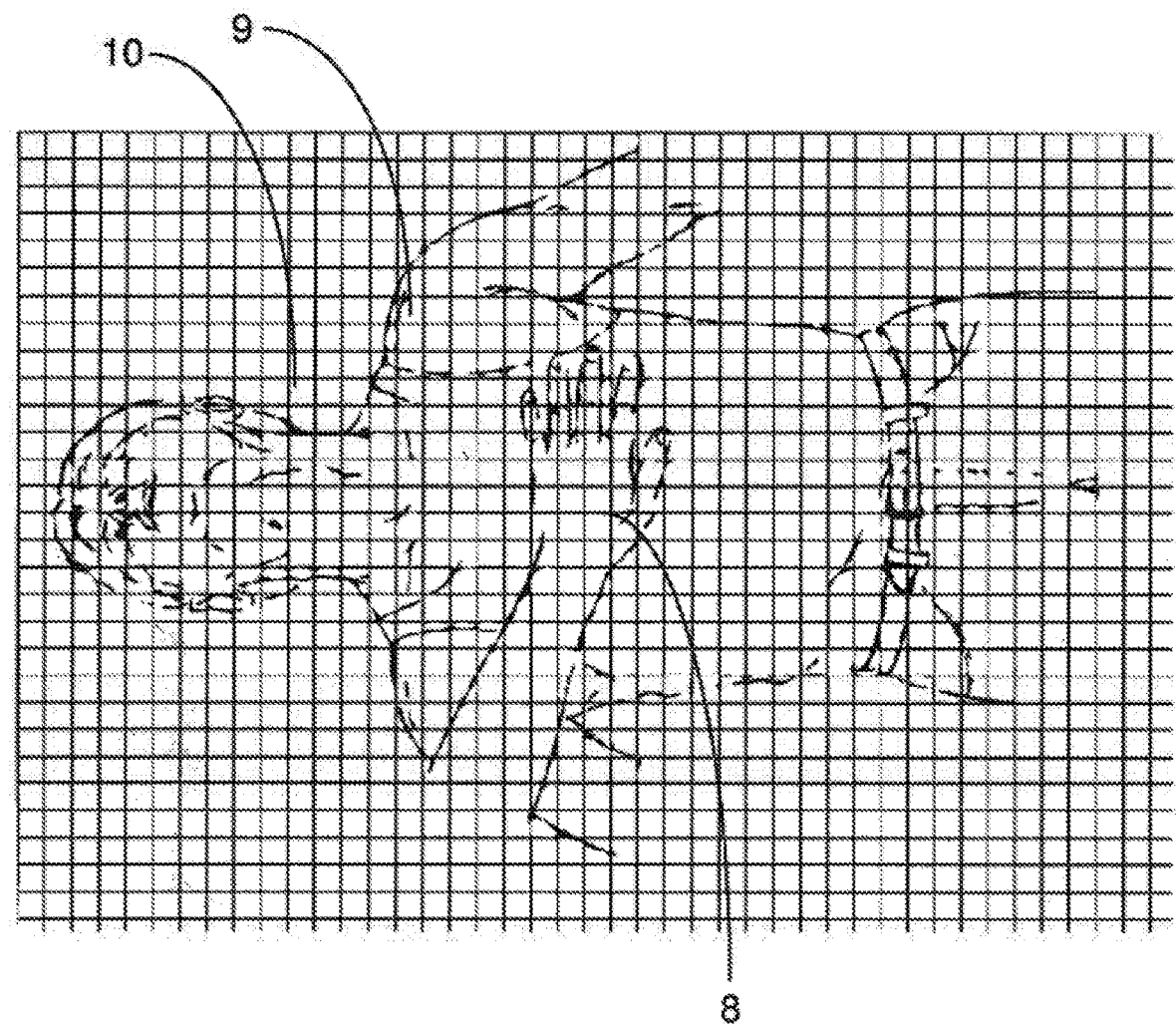
FIG. 4 shows an example of a compression gradient according to embodiments of the invention.
Figure 5:
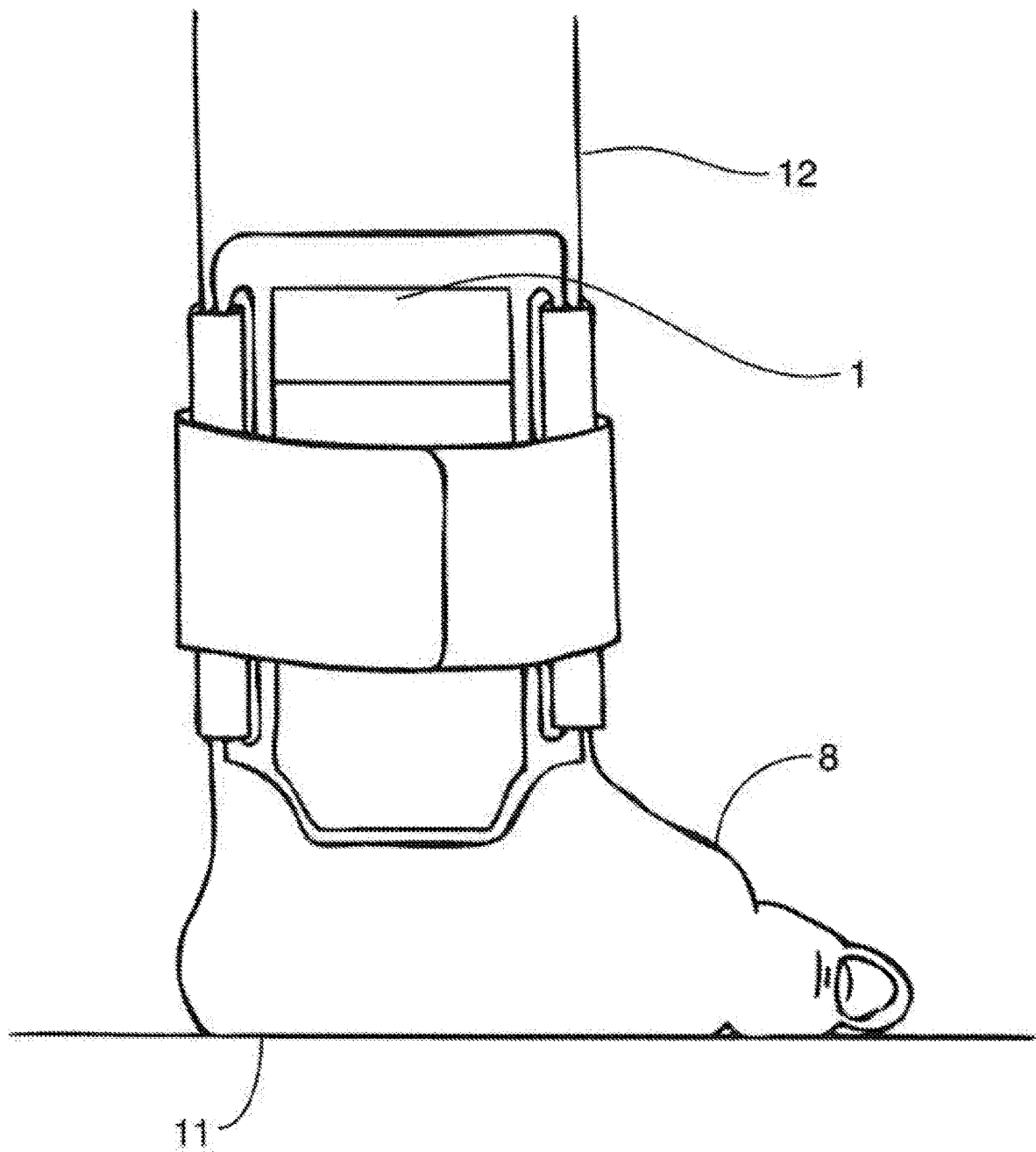
FIG. 5 depicts a wearable embodiment of a three-dimensional image sensor in which the sensor is attached to the arm of the rescuer according to embodiments of the invention.

The time-of-flight distance data is used to construct a compression gradient, a representation of which is shown in FIG. 4. A compression gradient is a detailed three dimensional map of the rescuer's hand 8, a portion of the victim's body 9 and preferably a portion of the ground beneath the victim 10. This compression gradient is important to extracting the depth information of each chest compression. Infrared light 3 is emitted from an illumination source 2 or multiple illumination sources adjacent to the image sensor 1. The light is invisible to the naked eye and generally immune to ambient interference. When affixed to the arm of the rescuer as shown in FIG. 5, the image sensor 1 receives the infrared light 3 reflected from the victim's body and the ground. A chest compression compresses the ribs, sternum and chest of the victim but generally leaves the stomach, neck and head of the victim substantially unmoved. Furthermore, the ground 10 or surface beneath the victim generally remains stationary during a compression. The system including the sensor 1 makes a determination of the quality of a compression by analyzing the generated gradient. The stationary portions of the victim and ground 10 will move closer to the sensor as the compression progresses downward. However, the hands of the rescuer 8 as well as the portion of the chest of the victim 11 adjacent and under the hand of the rescuer will remain stationary relative to the sensor. Therefore, the hands of the user 8 and chest of the victim 11 will appear deeper in the gradient than the stationary portions of the image. Once the rescuer's hand reaches the bottom of the compression, it will begin to move upward again and the stationary parts of the victim and the ground will appear to move away from the sensor. This gradient information can be used to accurately determine the depth of the compression.

At the start of the chest compression, the stationary aspects of the image will be furthest away from the image sensor. As the compression travels deeper, those stationary aspects such as the ground 10 and victim's anatomy will travel toward the sensor. Therefore, the algorithm continually searches for stationary aspects by finding adjacent pixels of a similar distance. The on-board processor isolates these blocks and tracks their distance relative to the arm 12 of the rescuer on which the sensor resides. If the image sensor 1 finds an area of ground beneath 10 the victim, it will track the distance of the ground relative to the sensor. If it finds a portion of the victim's stomach, it will track the distance of the stomach relative to the sensor. Any nonmoving surface may provide a suitable reference point.

Figure 6:
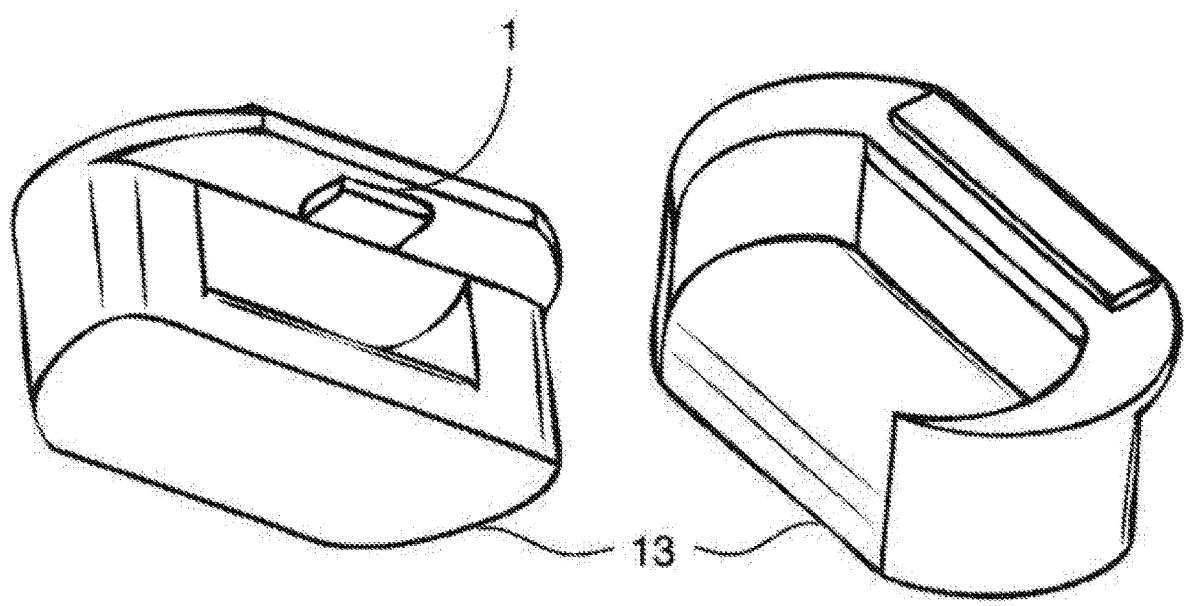
FIG. 6 shows an external block housing a three-dimensional image sensor that may be placed under and around the hands of the rescuer during the administration of CPR according to embodiments of the invention.
Figure 7:
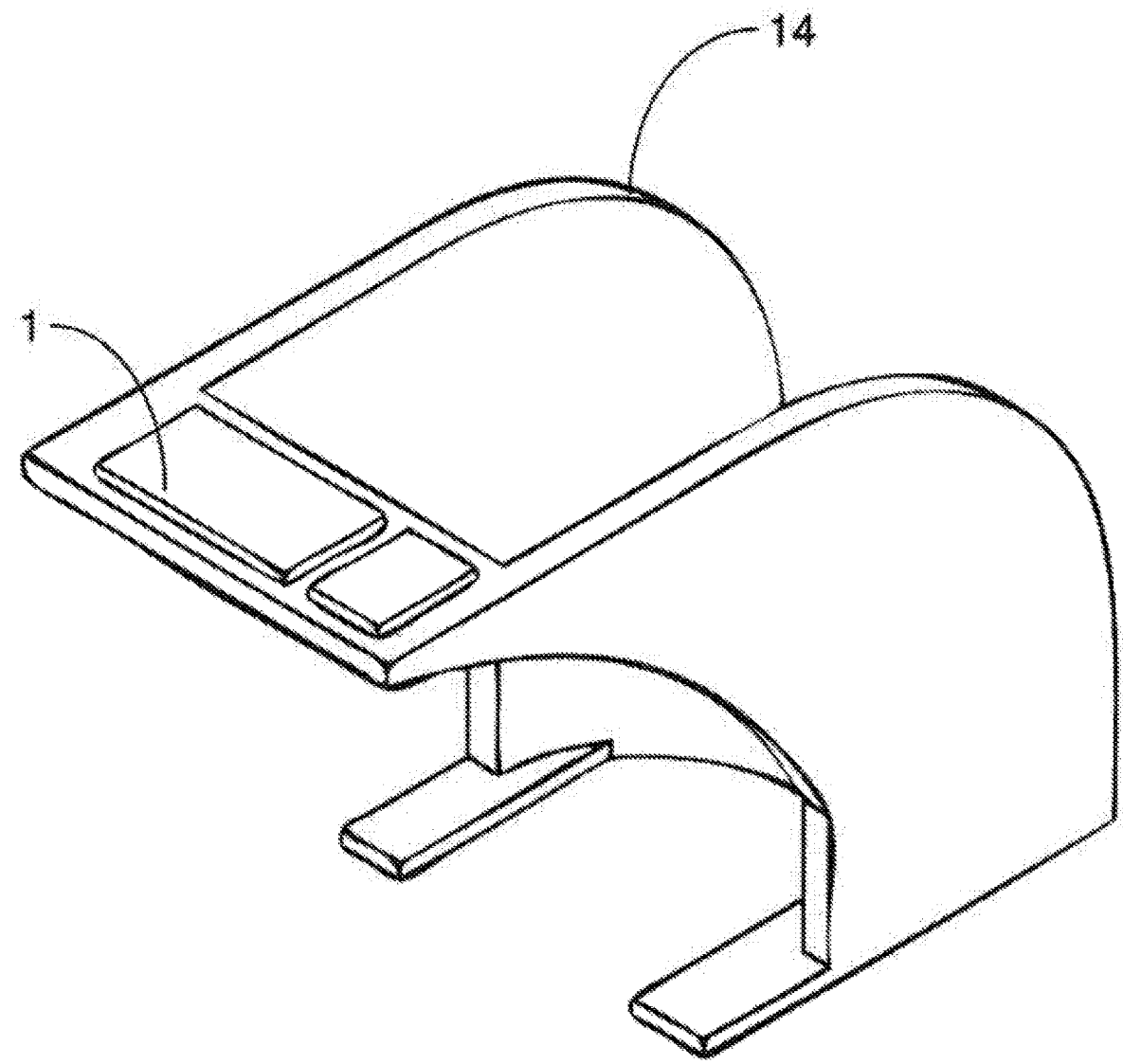
FIG. 7 shows an external support stand housing a three-dimensional image sensor that may be positioned over the victim's torso according to embodiments of the invention.
Figure 8:
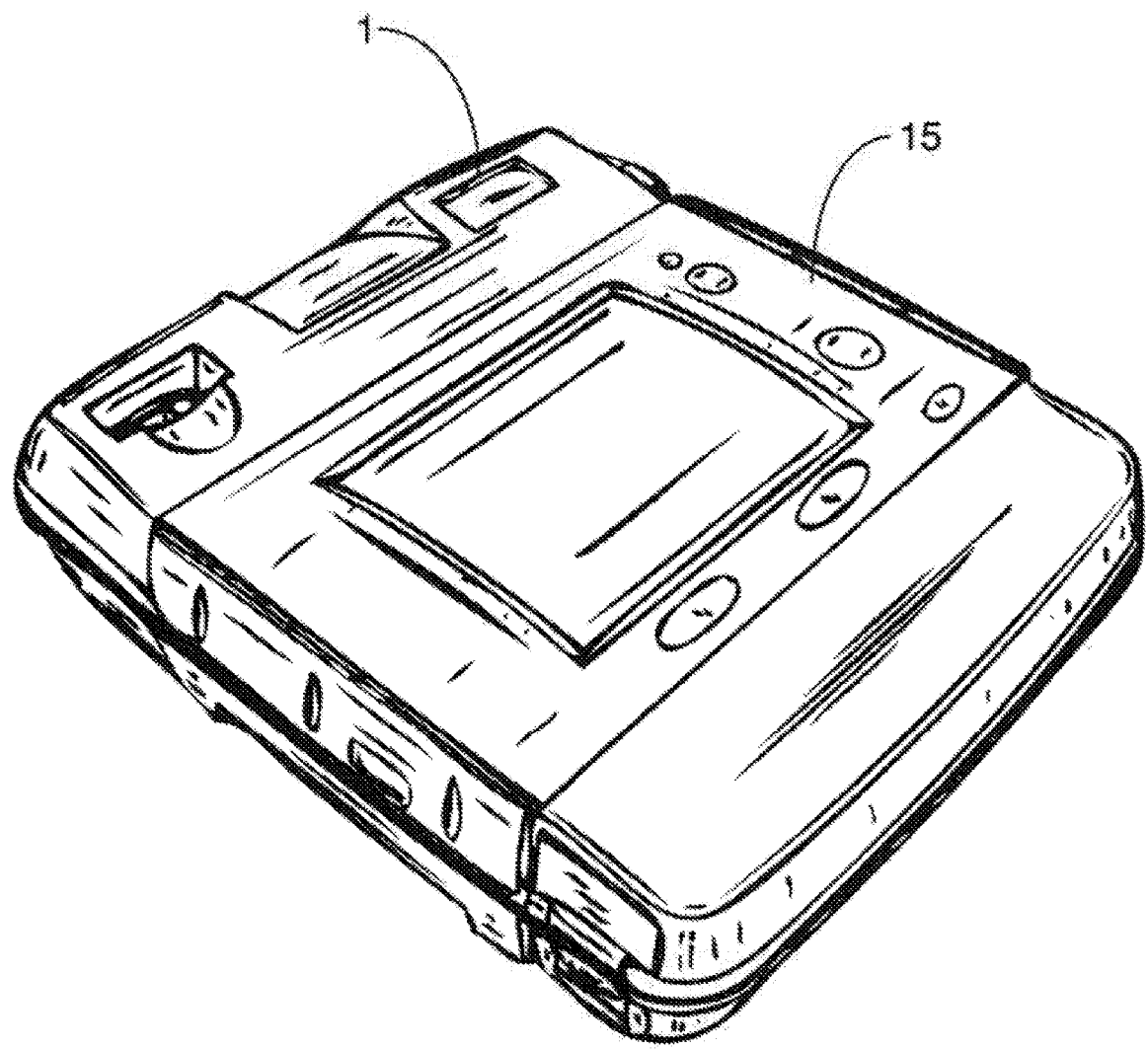
FIG. 8 shows an automatic external defibrillator that may house a three-dimensional image sensor according to embodiments of the invention.
Figure 9:
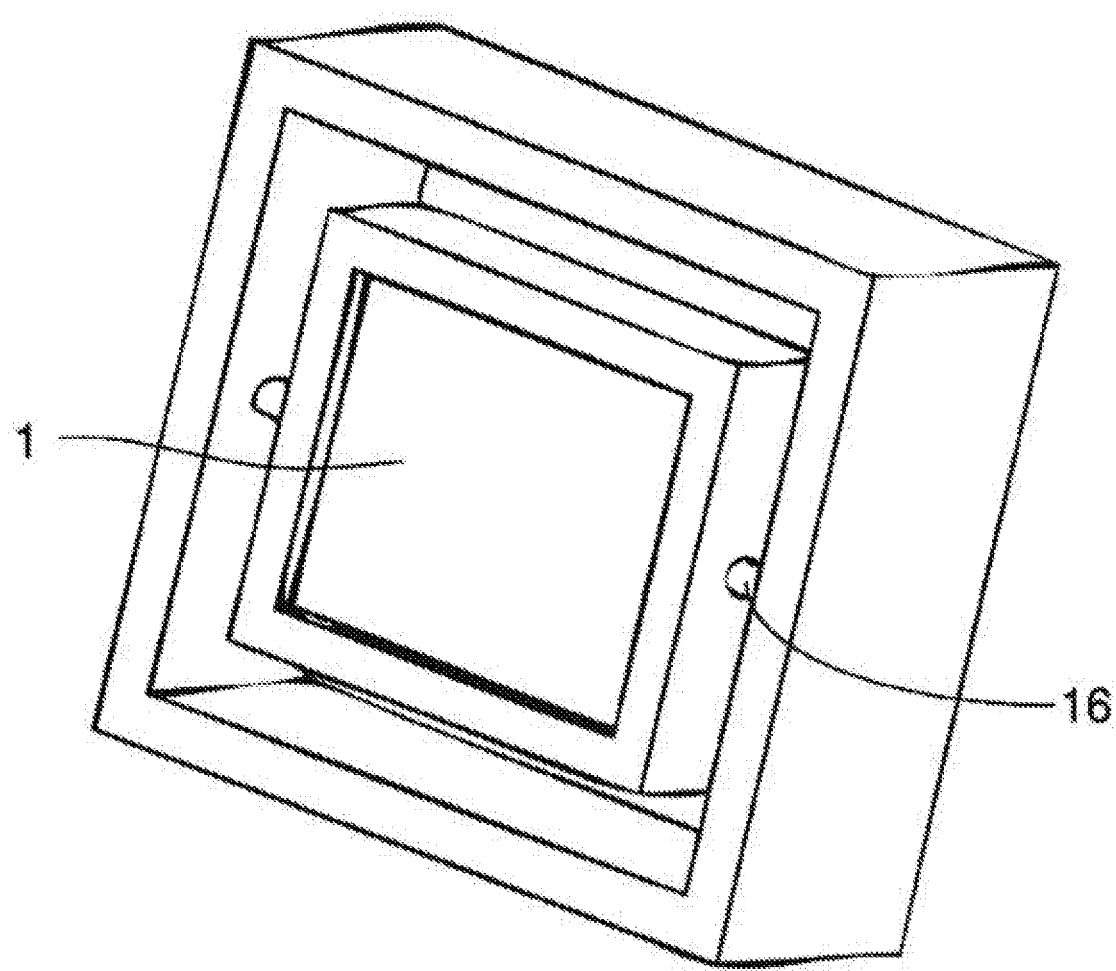
FIG. 9 illustrates a three-dimensional image sensor on a swinging pivot according to embodiments of the invention.

The image sensor 1 may be mounted on the arm 12 of the rescuer, as discussed above, or may be mounted inside a device 13 partially or fully under or around the rescuer's hands as show in FIG. 6. The sensor 1 may instead be mounted above the body of the victim using an external support or stand 14 as shown in FIG. 7. The image sensor 1 can also be placed in an external unit 15 beside the patient, such as a defibrillator, that is positioned so that the image sensor 1 may monitor the compression as shown in FIG. 8. The sensor 1 may also be placed on a pivot 16 to ensure that is constantly points in the same direction and is not affected by unpredictable movements of the rescuer's arm 12 or the victim's body 9 as shown in FIG. 9.

The image sensor 1 used may be a three dimensional time-of-flight CMOS sensor fabricated for the purpose of distance determination as seen in U.S. Pat. No. 6,323,942, which is incorporated by reference herein. Certain suitable sensors currently on the market include the CANESTAVISION PERCEPTION chipset from Canesta, the PHOTON ICs from PMD Technologies GmbH, and the SWISSRANGER sensors from Mesa Imaging. The three-dimensional imaging may also be accomplished by stereo vision through the algorithmic processing and combining of the input from two distinct image sensors.

B. Optical Flow Measurement

Figure 10:
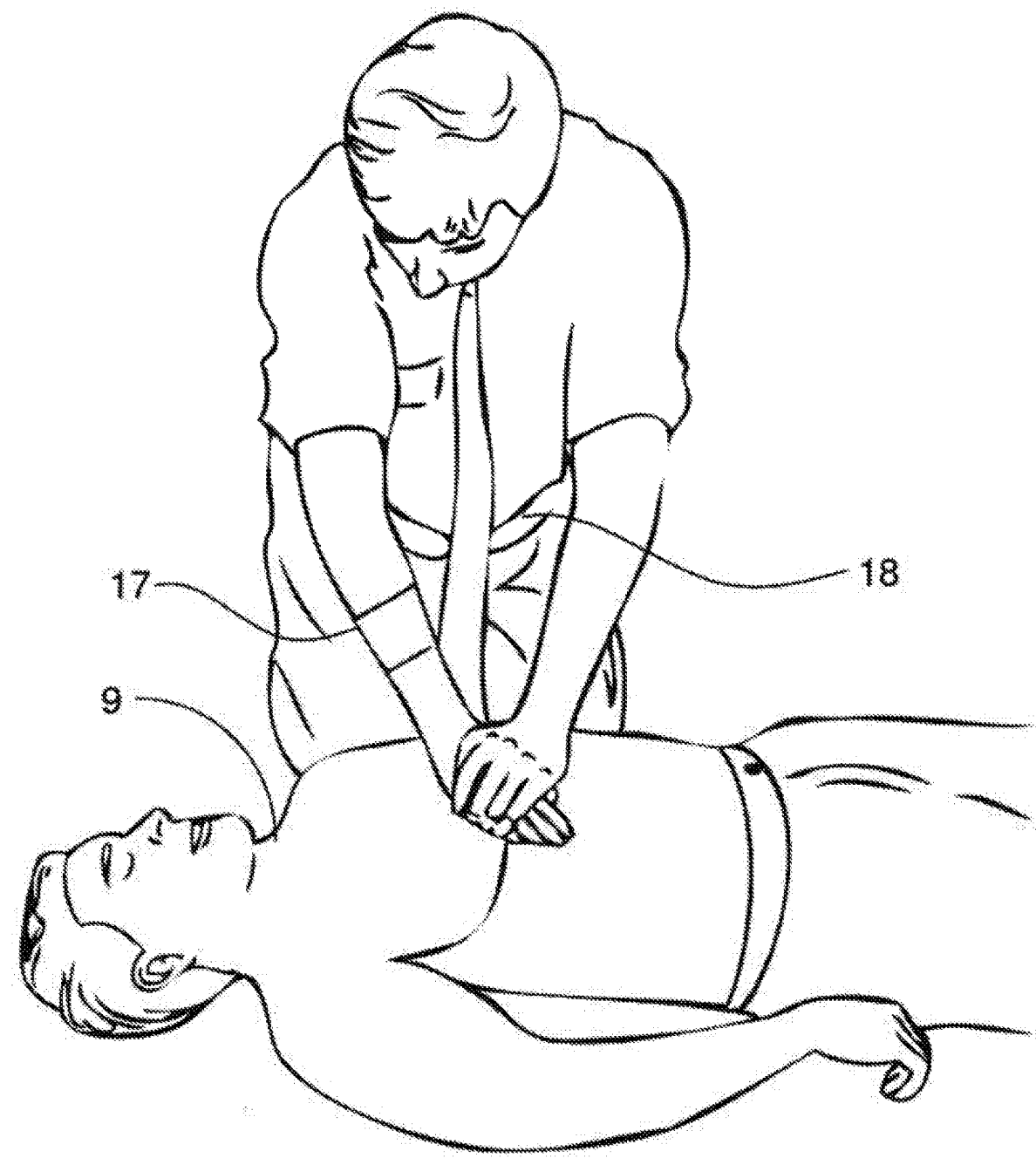
FIG. 10 depicts an image sensor affixed the arm of a rescuer for the determination of optical flow according to embodiments of the invention.

Another method of determining compression depth involves the use of optical flow techniques in which an image sensor monitors the surrounding environment to track the movement of textures and patterns. The image sensor may be mounted on the posterior surface of the forearm 17 of the rescuer and aimed at the torso 18 of the rescuer as shown in FIG. 10. As the compression is initiated, the sensor will move downward, but the torso 18 of the rescuer will generally remain stationary. Therefore, the image sensor 1 will monitor patterns or unique aspects of the torso 18 of the rescuer and correlate the movement of these patterns to the movement of the sensor 1 and thus the movement of the rescuer's arm 12. The depth of a chest compression can then be determined by relating the movement of the rescuer's arm to the movement of the victim's chest.

This method employed for the optical flow technique is similar to that found in optical computer mice that employ an image sensor for tracking the patterns and features of the surface on which the mouse is used. Using a relatively high resolution image sensor, distinct features may be tracked at a very high frame rate. As the feature moves past the image sensor, a distance is calculated based on the frame rate and distance travelled of that specific feature being tracked. This distance and speed is then translated into the speed and distance travelled by the rescuer's hand through the entirety of the chest compression.

GENERATION OF A COMPRESSION GRADIENT

During the calculation of most CPR related parameters using time-of-flight three dimensional image sensors, a compression gradient or similar depth map may be generated by, for instance, the processing circuitry.

The time-of-flight distance data from the image sensor is used to construct a compression gradient. A compression gradient is a detailed three dimensional map of the rescuer's hand, a portion of the victim's body and preferably a portion of the ground beneath the victim. This compression gradient is a base for extracting the depth information of each chest compression.

Figure 11:
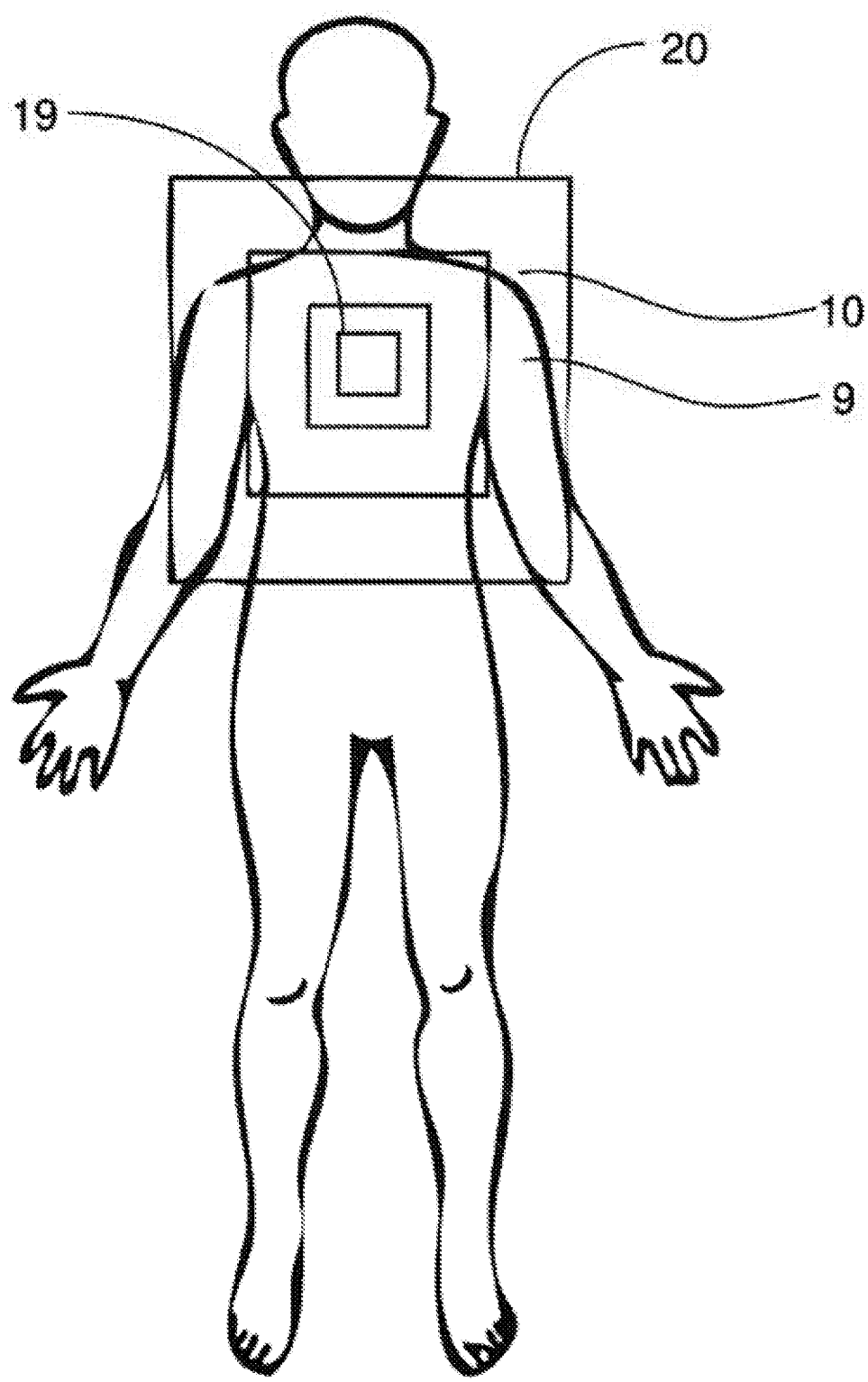
FIG. 11 illustrates the isolation of various regions of the victim from the effects of a chest compression according to embodiments of the invention.

The compression gradient consists of a contour map of the victim's body originating at the site of the chest compression and radiating outward. The pixels of the image sensor visualizing an area closest 19 to the site of the compression will be most affected by the compression itself and the pixels visualizing an area furthest 20 from the site of the compression will be least affected by the compression as shown in FIG. 11. In a preferred embodiment, the image sensor will move with the rescuer's hands through the entire distance of the compression and, consequently, the pixels nearest to the site of the compression should measure a constant or nearly constant depth. The pixels furthest away from the site of the compression should measure the largest change in depth as they will be moving toward the sensor as the compression progresses downward and away from the sensor as the compression is released. Therefore, the pixels furthest away from the site of the compression are deemed to be the stationary components of the scene (the victim's shoulders, the ground beneath the victim, etc.)

Therefore, a compression gradient is a depth contoured map of the victim's body 9, the ground 10 or surface beneath the victim and a portion of the hands 8 of the rescuer at the site of the compression. The compression gradient shows the distance or relative distance from the image sensor to the victim and ground at any instance in time for every pixel in the sensor. A processor or controller weighs the importance of that pixel's information by how isolated it is from the incident site of the compression. If a certain set of pixels is imaging the ground around the victim, for example, the processor determines that this is an important stationary reference point that can be used to calculate the depth of the chest compressions. Stationary points in the environment appear to move relative to the image sensor as it travels during the course of the chest compression. It is these stationary reference points that allow compression depth to be most precisely calculated.

An example method of generating a compression gradient is illustrated in FIG. 18. In the illustrated method, a starting or baseline image is obtained by the sensor 1 in a process 50. Then a compression begins in a process 52. A distance between the sensor and the image viewing area of the sensor is tracked during the chest compression in a process 54, and, in a process 56, a gradient is calculated based on the data generated by the image sensor. In some embodiments data from a timer may be used as well.

DETERMINATION OF COMPRESSION RATE

Calculating the rate of compressions delivered during the administration of CPR may be accomplished with the use of an image sensor 1. The generation of a compression gradient with time-of-flight principles allows for the determination of the initiation and termination of a single chest compression. A processor or controller may determine when a chest compression has passed through both its maximum and minimum depths and may register this as a single event. Therefore, a device using an image sensor as a compression monitor may indicate to the rescuer at what rate the CPR is being performed and how many chest compressions may be remaining in a certain chest compression cycle. International guidelines indicate that CPR should be performed at a rate of 100 compressions per minute and that there should be thirty compressions for every two breaths in each cycle.

An example method of determining a compression rate is illustrated in FIG. 19. In the illustrated method, a starting or baseline image is obtained by the sensor 1 in a process 60. Then a compression begins in a process 62. At the time of the maximum compression, a timer state is recorded in a process 64, and the timer state at a moment of maximum release is also recorded in a process 66. In a process 68, a processor uses the relative times from the maximum and minimum times to generate a rate of chest compressions, or CPR rate, The processes 64-68 may be repeated to generate an average compression rate.

DETERMINATION OF COMPRESSION ANGLE

Figure 12:
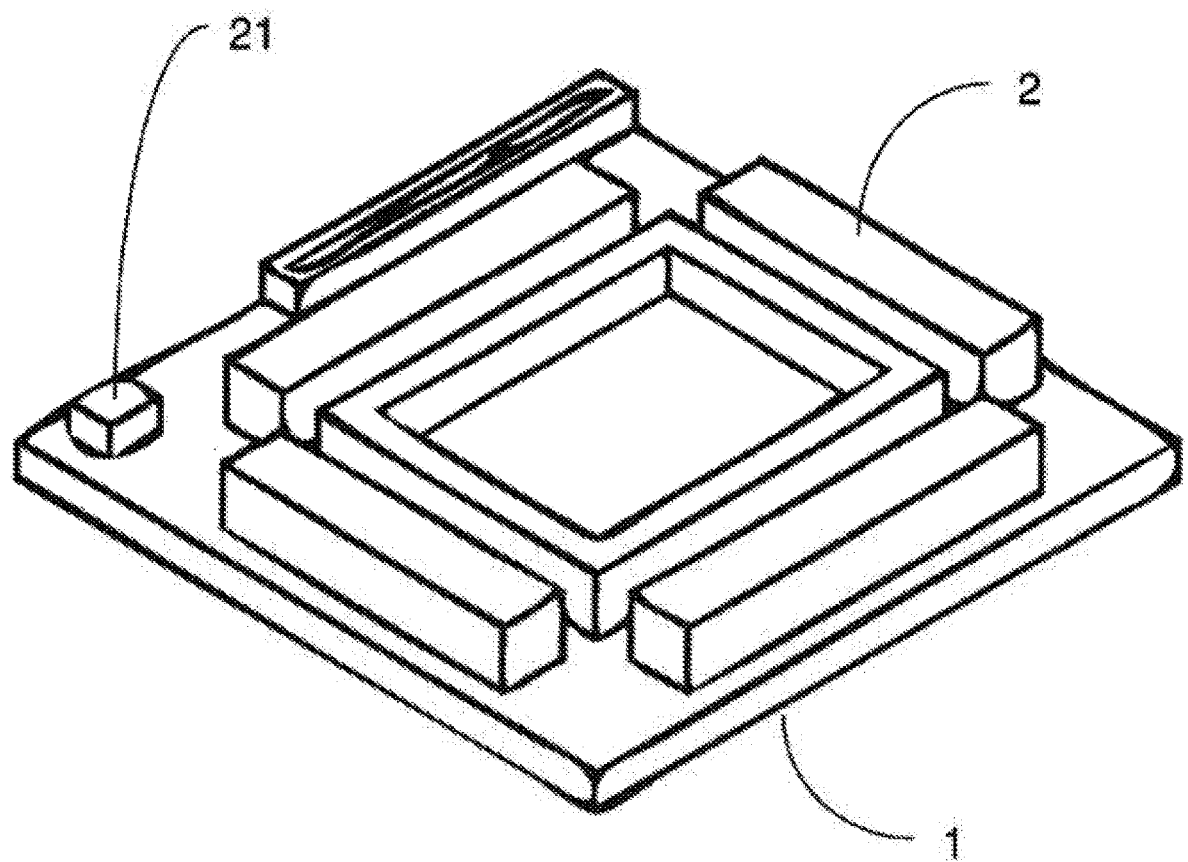
FIG. 12 shows an accelerometer adjacent to an image sensor for the determination of compression angle according to embodiments of the invention.

Compression angle 22 may be monitored by placing an accelerometer 21, tilt sensor or other device alongside the image sensor in a CPR assist device as shown in FIG. 12. The compression angle sensor would enable the CPR assist device to alert the rescuer if he or she must adjust his or her arms to achieve a proper chest compression angle. When delivering effective CPR, the hands of the rescuer 8 should be approximately perpendicular to the arms of the rescuer 12 as shown in FIG. 13. Furthermore, ensuring that the arms are perpendicular to the chest of the victim will help make certain that the image sensor is properly oriented. In the case that the arms are not at a right angle to the victim's chest, the sensor and infrared light source 2 can be placed on a swinging pivot 16 that changes it direction to compensate for the angle of the arms.

Compression angle may be determined by the image sensor 1 itself. If the image sensor 1 is affixed to the arm of the rescuer 12, trigonometric calculations may be used to determine the angle 22 that the sensor is oriented relative to a level, planar surface such as the ground 10 beneath the victim. The distances between the various pixels of the image sensor 1 and objects within the environment can be determined and compared. Relative to the ground or some level surface, an angle of compression can be easily determined.

DETERMINATION OF PROPER CPR HAND POSITION

Proper hand placement during CPR is vital to restoring circulation to the victim. If the rescuer's hands are not appropriately positioned over the sternum of the victim, the CPR will not be performed at its maximum efficiency and injury may result. Therefore, the determination of proper hand placement is vital to the delivery of accurate and efficient CPR.

Correct CPR hand position 23 is determined by locating a position approximately two inches directly above the victim's xyphoid process 24 where the lower ribs meet the sternum as shown in FIG. 14. The rescuer's hands 8 should be centered laterally on the chest between the shoulders 25 of the victim. In order to determine the lateral centering 26, the image sensor 1 may calculate the distance between the opposing shoulders 25 of the victim and easily conclude the center 26 from this information. The location of the xyphoid process 24 is substantially more difficult and relies on a calculation of the overall size of the patient, as explained below. Once the approximate size of the patient is determined, the position of the victim's ribs and xyphoid process 24 may be interpolated, allowing the sensor to determine if the rescuer's hands 8 are in the general locale of the sternum. Rather than precisely indicating position to the rescuer, the device will alert the user if his or her hand position is clearly off mark by a statistically significant amount.

An example method of determining proper hand placement is illustrated in FIG. 20. In the illustrated method, a starting or baseline image is obtained by the sensor 1 in a process 70. Then a hand position of the rescuer is determined by analyzing data and/or images from the image sensor in a process 72. A process 74 locates the xyphoid process of the patient, or an area near the xyphoid process, and a process 76 determines if the hand position of the rescuer is near the appropriate position of the xyphoid process of the victim. The determination of hand position may be related back to the rescuer in a process 78.

DETERMINATION OF VICTIM BODY TYPE

An image sensor for detection of compression depth may also have the inherent capability of determining body size and body type as shown in FIG. 15. An image sensor 1 suspended above the victim's body 9 may locate the contours 27 of the body, as well as its size and the depth 28 to the ground beneath it.

Suspended above the victim's body, the image sensor 1 is capable of determining specific parameters related to the body type of the victim. Such parameters include shoulder to shoulder width 29, torso length 30, depth of chest to ground 28, arm length 31, neck width 32 and others. By uniquely combining these elements, it is possible to determine the approximate size of the victim. Upon determination of the victim body type, the CPR protocol may be adjusted accordingly.

The determination of body type is especially important in child and infant CPR where the depth of compressions should be directly correlated to the depth of the chest of the child. For example, if compressions should be one-third to one-half the total anteroposterior diameter of the chest, the image sensor can quickly calculate this dimension and ensure that the advised compression depth is in accordance with the child's size. This will ensure that CPR is delivered appropriately for a victim of any body size from the smallest infant to the largest adult.

An example method of determining patient body type is illustrated in FIG. 21. In the illustrated method, a patient image is gathered by the sensor in a process 80. A process 82 determines patient parameters from the image, such as shoulder width, torso length, depth of chest to ground, arm length, neck width, etc. Then, one or more of the parameters are compared to a database or history of previously stored parameters or set of comparisons or determinations in a process 84. This comparison or determination allows the system to determine the proper body type.

DETERMINATION OF EFFECTIVE RESCUE BREATHING

The image sensor may be used for the detection of chest rise 33 during the administration of artificial respiration as shown in FIG. 16. If suspended above the patient, a three dimensional gradient may be generated similar to a compression gradient. This gradient may be used to determine if the chest of the victim rises during rescue breathing and to what extent the chest rises. This information may be used to determine if a successful breath has been administered. Such methods are illustrated in FIG. 22. In that figure, a starting image is recorded in process 90 and a gradient is generated in process 92 based on the chest rising due to rescue breaths, as described above. Data about the rescue breaths is recorded in process 94, such as the amount of the victim's chest rising and the amount of time between rescue breaths. The collected data is compared to stored data in a process 96, which may then determine if the rescue breathing is effective.

DETERMINATION OF CHEST RECOIL

The image sensor may also be used to determine if the chest has completely recoiled during the administration of CPR. After a chest compression attains the desired depth, the victim's chest should be released fully and completely before commencing the next compression. A compression gradient may be used to determine if the chest has been allowed to fully recoil by measuring the depth of the rescuer's hands 8 relative to the victim's torso 9 and ground 10.

POTENTIAL EMBODIMENTS

The measurement of compression depth with optical sensors may be employed in various embodiments not limited by the specifications disclosed herein. For example, the sensor may be wearable in the form of a glove, wrist band shown in FIG. 17, wrist guard shown in FIG. 5 or any other type of garment on the rescuer. The sensor may also be housed in a solid block, pad or similar device placed beneath the hands of the rescuer. The sensor may be placed on an independent support or stand to be suspended above the patient. The sensor may also be placed within another piece of equipment, such as a defibrillator.

When configured in a block or pad, the optical sensor should be elevated above the chest of the victim so that it may image a large enough portion of the victim's chest and the ground beneath the victim. The sensor may be configured so that it is raised above the hands of the rescuer and body of the victim. When configured in an external support or stand, the sensor may be elevated high above the victim and rescuer allowing visualization of a larger portion of the ground, victim's body and rescuer's hands. The stand may be completely independent of the victim and rescuer and may be positioned adjacent to the victim so that the image sensor is elevated and suspended above the victim.

In embodiments of the invention, the device may have a method of feedback or the methods may incorporate feedback within them. For example, if the image sensor is placed within a block, a numerical or graphical display 34 may be embedded opposite the sensor so that visual data is relayed to the rescuer. Furthermore, audio feedback may be embedded into the device to complement or replace the visual feedback. In many embodiments of the invention, there is an optical sensor used to image a portion of the victim or rescuer. In the preferred embodiment of three-dimensional time-of-flight sensors, the optical sensor is pointed downward, toward the victim, to allow for optimal visualization of the victim, ground and rescuer's hands. Ultimately, the generation of a compression gradient allows for the determination of most crucial CPR related parameters.

What is claimed is:

1. A device for monitoring chest compressions during the administration of Cardiopulmonary Resuscitation (CPR) to a patient, comprising:

an optical sensor having a field of view of an environment that includes at least a portion of a chest of the patient and is configured to:
receive reflected light, the reflected light reflected from one or more components in the environment; and
generate output data based, at least in part, on the reflected light; and
a processor configured to:
receive the output data,
identify the one or more components in the environment based on the output data,
determine a change in distance over time between the optical sensor and each of the one or more components in the environment based on the output data,
identify a substantially stationary component in the environment based on the change in distance over time between the optical sensor and each of the one or more components in the environment,
calculate a compression depth of the chest of the patient based on the substantially stationary component in the environment and the change in distance over time between the optical sensor and each of the one or more components in the environment, and
output the compression depth to a display coupled to the device.

2. The device for monitoring chest compressions according to claim 1, in which the processor is further configured to determine a compression rate from the received output data and to output the compression rate to the display.

3. The device for monitoring chest compressions according to claim 1, wherein the optical sensor is configured to detect a position of an object in three-dimensional space, and wherein the object includes the at least a portion of the chest of the patient.

4. The device for monitoring chest compressions according to claim 1, wherein the field of view of the optical sensor includes the at least a portion of the chest of the patient and at least a portion of a stationary object in the environment.

5. The device for monitoring chest compressions according to claim 1, in which the processor is integrated into the optical sensor.

6. The device for monitoring chest compressions according to claim 1, in which the processor is integrated into a defibrillator.

7. The device for monitoring chest compressions according to claim 1, in which the display is integrated into a defibrillator.

8. The device for monitoring chest compressions according to claim 1, in which the optical sensor is included in a sensor block that also includes an accelerometer.

9. The device for monitoring chest compressions according to claim 1, further comprising an infrared light emitter configured to illuminate the environment.

10. An external defibrillator system, comprising:
an input electrically coupled to an optical sensor and configured to receive data output from the optical sensor, the optical sensor configured to:
generate reflected light data based, at least in part, on light reflected from one or more components in an environment about the optical sensor during movement of at least a portion of a chest of a patient during CPR administration;
a display structured to provide CPR feedback information to a user; and
a processor configured to:
receive the reflected light data,
determine changes in distance over time between the one or more components in the environment and the optical sensor based on the reflected light data,
identify a substantially stationary component in the environment based on the changes in distance over time between the one or more components in the environment and the optical sensor,
calculate a compression depth of the chest of the patient during the CPR based on the substantially stationary component in the environment and the one or more changes in distance over time between the one or more components in the environment and the optical sensor, and
cause the defibrillator to numerically display the compression depth on the display.

11. The external defibrillator according to claim 10, in which the processor is further configured to determine a compression rate based on the reflected light data and to cause the defibrillator to display the compression rate.

12. The external defibrillator according to claim 11, in which the optical sensor is included in the defibrillator.

13. The external defibrillator according to claim 10, in which the stationary component in the environment includes the at least a portion of the chest of the patient.

14. The external defibrillator according to claim 10, wherein the optical sensor is configured in a block, the block configured to be placed beneath the hands of a rescuer.

15. A method for providing feedback information about chest compressions during the administration of Cardiopulmonary Resuscitation (CPR) to a patient, the method comprising:
illuminating an environment that includes at least a portion of a chest of the patient and at least a portion of an area about the patient;
detecting reflected light with an optical sensor, the reflected light reflecting from the at least a portion of the chest of the patient and the at least a portion of the area about the patient;
generating reflected light data based on the detected reflected light;
determining one or more changes in distance between the optical sensor and one or more components in the environment based on the reflected light data;
identifying a substantially stationary component in the environment based on the one or more changes in distance between the optical sensor and the one or more components in the environment;
calculating a compression depth of the chest of the patient during the CPR based, at least in part on, the stationary component and the one or more changes in distance between the optical sensor and one or more components in the environment; and
displaying the compression depth as a numerical value on a display.

16. The method for providing feedback information according to claim 15, further comprising determining a compression rate from the reflected light data.

17. The method for providing feedback information according to claim 16, further comprising causing a defibrillator to display the compression rate.

18. The method for providing feedback information according to claim 15, in which the optical sensor is included in a sensor block that includes an accelerometer.

19. The method for providing feedback information according to claim 15, wherein the optical sensor is included in a defibrillator.

20. The method for providing feedback information according to claim 15, wherein the optical sensor is configured in a block, the block configured to be placed beneath the hands of a rescuer.

\* \* \* \* \*